(12) United States Patent
Fliss et al.

(10) Patent No.: US 9,642,362 B2
(45) Date of Patent: May 9, 2017

(54) ANTIMICROBIAL COMPOSITIONS AND USES THEREOF

(71) Applicant: CASCADES CANADA ULC, Montreal (CA)

(72) Inventors: Ismail Fliss, Québec (CA); Pierre Hudon, La Prairie (CA); Marie-Helene Charest, Kingsey Falls (CA); Nathalie Comeau, Candiac (CA)

(73) Assignee: CASCADES CANADA ULC, Montreal (CA)

( * ) Notice: Subject to any disclaimer, the term of this patent is extended or adjusted under 35 U.S.C. 154(b) by 0 days.

(21) Appl. No.: 14/395,056

(22) PCT Filed: Apr. 15, 2013

(86) PCT No.: PCT/CA2013/050290
§ 371 (c)(1),
(2) Date: Oct. 16, 2014

(87) PCT Pub. No.: WO2013/155624
PCT Pub. Date: Oct. 24, 2013

(65) Prior Publication Data
US 2015/0072920 A1 Mar. 12, 2015

Related U.S. Application Data

(60) Provisional application No. 61/782,453, filed on Mar. 14, 2013, provisional application No. 61/624,611, filed on Apr. 16, 2012.

(51) Int. Cl.
| | | |
|---|---|---|
| *A01N 37/46* | (2006.01) | |
| *B65B 55/00* | (2006.01) | |
| *A23L 3/3499* | (2006.01) | |
| *A23L 3/3526* | (2006.01) | |
| *A01N 35/04* | (2006.01) | |
| *A01N 37/02* | (2006.01) | |
| *A23L 3/3508* | (2006.01) | |
| *A01N 37/36* | (2006.01) | |
| *A01N 63/02* | (2006.01) | |
| *A23L 3/3463* | (2006.01) | |
| *A61L 2/00* | (2006.01) | |

(52) U.S. Cl.
CPC ............ *A01N 37/46* (2013.01); *A01N 35/04* (2013.01); *A01N 37/02* (2013.01); *A01N 37/36* (2013.01); *A01N 63/02* (2013.01); *A23L 3/3499* (2013.01); *A23L 3/34635* (2013.01); *A23L 3/3508* (2013.01); *A23L 3/3526* (2013.01); *B65B 55/00* (2013.01); *A23V 2002/00* (2013.01); *A61L 2/0005* (2013.01); *A61L 2202/23* (2013.01)

(58) Field of Classification Search
None
See application file for complete search history.

(56) References Cited

U.S. PATENT DOCUMENTS

| | | | |
|---|---|---|---|
| 4,597,972 A | 7/1986 | Taylor | |
| 4,883,673 A | 11/1989 | Gonzalez | |
| 5,186,962 A | 2/1993 | Hutkins et al. | |
| 5,217,950 A | 6/1993 | Blackburn et al. | |
| 5,573,800 A * | 11/1996 | Wilhoit ................... | A23B 4/22 |
| | | | 426/133 |
| 5,573,801 A | 11/1996 | Wilhoit | |
| 6,207,210 B1 | 3/2001 | Bender et al. | |
| 6,991,820 B2 | 1/2006 | Ming et al. | |
| 7,001,632 B2 | 2/2006 | Nauth et al. | |
| 7,247,330 B2 | 7/2007 | Kuethe et al. | |
| 2005/0053593 A1 | 3/2005 | Wang et al. | |
| 2008/0152758 A1 | 6/2008 | Zheng et al. | |
| 2008/0152759 A1 | 6/2008 | Hong et al. | |
| 2009/0111894 A1 | 4/2009 | Bos et al. | |
| 2010/0129501 A1 | 5/2010 | Blommer et al. | |
| 2010/0239561 A1 | 9/2010 | Schobitz Twele et al. | |
| 2010/0284985 A1 | 11/2010 | Mygind et al. | |
| 2011/0053832 A1 | 3/2011 | Antoniewski et al. | |
| 2011/0236359 A1 | 9/2011 | Lacroix et al. | |

FOREIGN PATENT DOCUMENTS

| | | |
|---|---|---|
| EP | 0 384 319 A1 | 8/1990 |
| EP | 0 466 244 A1 | 1/1992 |

(Continued)

OTHER PUBLICATIONS

Kalchayanand et al. Letters in Applied Microbiology 1992, 15, 239-243.*
European Search Opinion for Application No. 13778929.3, dated Mar. 16, 2016.

(Continued)

*Primary Examiner* — Amber D Steele
*Assistant Examiner* — Schuyler Milton
(74) *Attorney, Agent, or Firm* — Marshall, Gerstein & Borun LLP

(57) ABSTRACT

The present invention relates to an antimicrobial composition having activity against Gram-positive and Gram-negative bacteria. The composition is a) a composition comprising at least two organic acids selected from the group consisting of lactic acid, acetic acid, benzoic acid and citric acid; b) a composition comprising at least two bacteriocin selected from the group consisting of pediocin, Nisin and reuterin; c) a composition comprising pediocin and at least two organic acids selected from the group consisting of lactic acid, acetic acid, benzoic acid and citric acid; or d) a composition comprising reuterin and at least one organic acid selected from the group consisting of lactic acid, acetic acid, benzoic acid and citric acid. The present invention also relates to the use of said compositions for sanitizing and/or disinfecting surfaces and method thereof.

13 Claims, 20 Drawing Sheets

(56) References Cited

FOREIGN PATENT DOCUMENTS

Figure 1A:
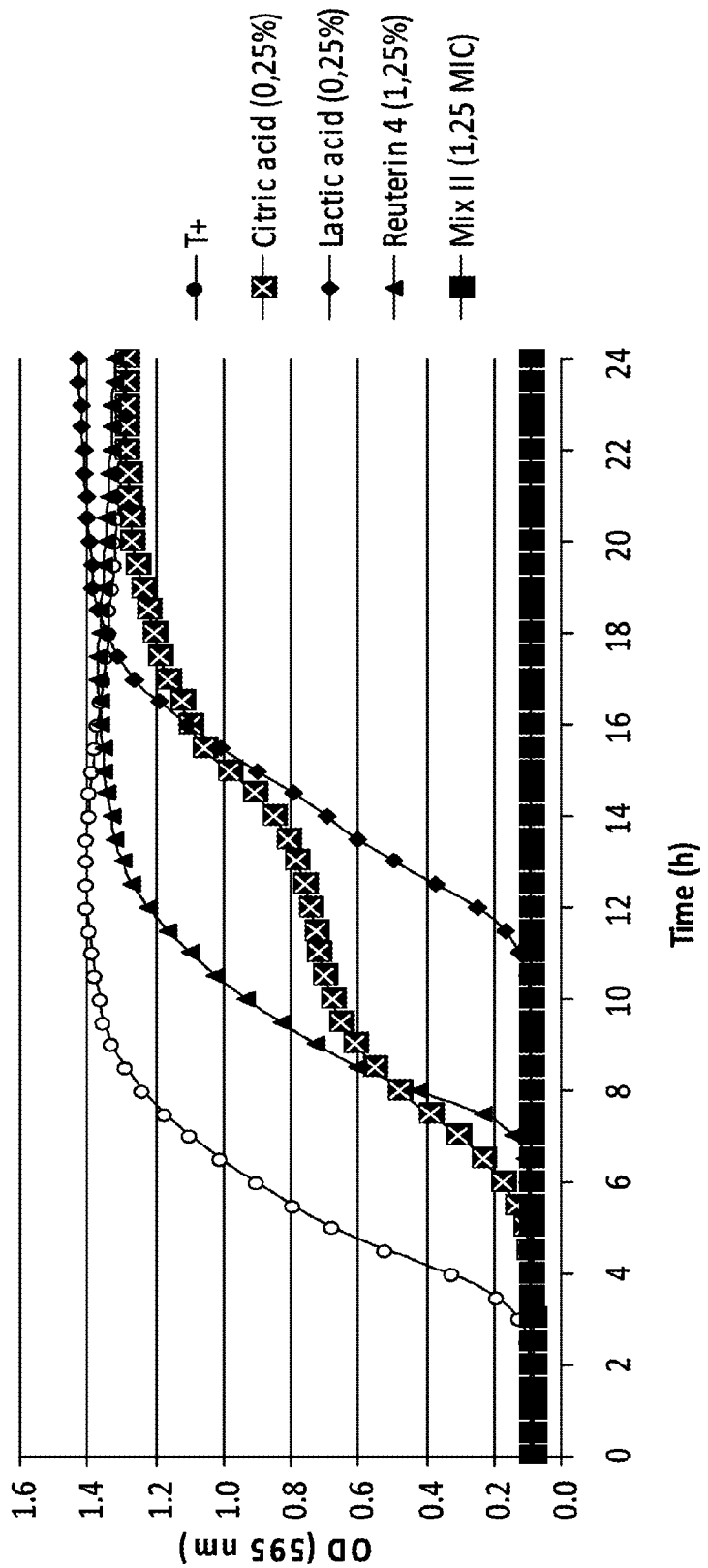

| | | |
|---|---|---|
| EP | 1 068 808 A1 | 1/2001 |
| EP | 1 369 045 A2 | 12/2003 |
| EP | 1 423 023 A2 | 6/2004 |
| EP | 2 289 350 A2 | 3/2011 |
| JP | 08-242831 A | 9/1996 |
| JP | H08280369 A * | 10/1996 |
| JP | 2007-312740 A | 12/2007 |
| WO | WO-88/08452 A1 | 11/1988 |
| WO | WO-96/39842 A1 | 12/1996 |
| WO | WO-00/69267 A1 | 11/2000 |
| WO | WO-2005/022998 A2 | 3/2005 |
| WO | WO-2005/104878 A1 | 11/2005 |
| WO | WO-2011/085499 A1 | 7/2011 |

OTHER PUBLICATIONS

Abee et al., "Pore-Forming Bacteriocins of Gram$^+$ Bacteria and Self-Protection Mechanisms of Producer Organisms," *FEMS Microbiol. Lett.*, 129:1-9 (1995).

Allende et al., "Growth and Bacteriocin Production by Lactic Acid Bacteria in Vegetable Broth and Their Effectiveness at Reducing *Listeria monocytogenes* in vitro and in Fresh-Cut Lettuce," *Food Microbiology*, 24(7):759-766 (2007).

Antimicrobal Susceptibility Testing Protocols. 2007, Kindle Edition Richard Schwalbe (Editor), Lynn Steele-Moore (Editor), Avery C. Goodwin (Editor) CRC Press, NY. Table of Contents only.

Arques et al., "Combined Effect of Reuterin and Lactic Acid Bacteria Bacteriocins on the Inactivation of Food-Borne Pathogens in Milk," *Food Control*, 22(3-4):457-461 (2011).

Bari et al., "Combined Efficacy of Nisin and Pediocin with Sodium Lactate, Citric Acid, Phytic Acid, and Potassium Sorbate and EDTA in Reducing the *Listeria monocytogenes* Population of Inoculated Fresh-Cut Produce," *Journal of Food Protection*, 68(7):1381-1387 (2005).

*Benebank*. Nucleic Acids Research, Jan. 2011; 39 (*Database Issue*): D32-7 AOAC International. 2000. AOAC Official Method 960.09. Germicidal and Detergent Sanitizing Action of Disinfectants.

Benech et al., "Antibacterial Activities of Nisin Z Encapsulated in Liposomes or Produced in situ by Mixed Culture During Cheddar Cheese Ripening," *Appl. Environ. Microbiol.*, 68(11):5607-5619 (2002).

Benson et al., GENBANK, Nucleic Acids Research, 39, Database Issue D32-37 (2011).

Brul et al., "Preservative Agents in Foods. Mode of Action and Microbial Resistance Mechanisms," *International Journal of Food Microbiology*, 50(1-2):1-17 (1999).

Cherrington et al., "Organic Acids: Chemistry, Antibacterial Activity and Practical Applications," *Advances in Microbial Physiology*, 32:87-108 (1991).

Cutter et al., "Improved Antimicrobial Activity of Nisin-Incorporated Polymer Films by Formulation Change and Addition of Food Grade Chelator," *Lett. Appl. Microbiol.*, 33:325-328 (2001).

Daba et al., "Influence of Growth Conditions on Production and Activity of Mesenterocin 5 by a Strain of *Leuconostoc Mesenteroides*," *Applied Microbiology and Biotechnology*, 39:166-173 (1993).

El-Ziney et al., "Application of Reuterin Produced by *Lactobacillus reuteri* 12002 for Meat Decontamination and Preservation," *Journal of Food Protection*, 62(3):257-261 (1999).

Ennahar et al., "Class IIa Bacteriocins: Biosynthesis, Structure and Activity," *FEMS Microbiology Reviews*, 24(1):85-106 (2000).

Fang et al., "Growth Patterns of *Escherichia* oil O157:H7 in Ground Beef Treated with Nisin, Chelators, Organic Acids and Their Combinations Immobiliized in Calcium Alginate Gels," *Food Microbiology*, 20:243-253 (2003).

Galvez et al., "Bacteriocin-Based Strategies for Food Biopreservation," *International Journal of Food Microbiology*, 120(1-2):51-70 (2007).

Glass et al., "Effects of Acid Type and ALTA™ 2341 on *Listeria monocytogenes* in a Queso Blanco Type of Cheese," *Journal of Food Protection*, 58(7):737-741 (1995).

Hammami et al., "BACTIBASE Second Release: A Database and Tool Perform for Bacteriocin Characterization," *BMC Microbiol.* (2010).

Hammami et al., "BACTIBASE: A New Web-Accessible Database for Bacteriocin Characterization," *BMC Microbiol.* (2007).

Hanlin et al., "Bacteriocins of Lactic Acid Bacteria in Combination Have Greater Antibacterial Activity," *Journal of Food Protection*, 56(3):252-255 (1993).

Helander et al., "Potential of Lactic Acid Bacteria and Novel Antimicrobials Against Gram-Negative Bacteria," *Trends in Food Science & Technology*, 8(5):146-150 (1997).

Kalchayanand et al., "Sublethal Injury Makes Gram-Negative and Resistant Gram-Positive Bacteria Sensitive to the Bacteriocins, Pediocin AcH and Nisin," *Letters in Applied Microbiology*, 15(6):239-243 (1992).

Le Blay et al., "In vitro Inhibition Activity of Nisin A, Nisin Z, Pediocin PA-1 and Antibiotics Against Common Intestinal Bacteria," *Letters in Applied Microbiology*, 45(3):252-257 (2007).

Mota-Meira et al., "MICs of Mutaciin B-Ny266, Nisin A, Vancomycin, and Oxacillin Against Bacterial Pathogens," *Antimicrob Agents Chemother.*, 44(1):24-29 (2000).

Naghmouchi et al., "Pediocin PA-1 Production During Repeated-Cycle Batch Culture of Immobilized *Pediococcus acidilactici* UL5 Cells," *J. Biosci. Bioeng.*, 105(5):513-517 (2008).

Nilsson et al., "Role of Acetate in Production of an Autoinducible Class IIa Bacteriocin in *Carnobacterium piscicola* A9b," *Appl. Environ. Microbiol.*, 68(5):2251-2260 (2002).

Nykänen et al., "The Effect Effect of Lactic Acid, Nisin Whey Permeate, Sodium Chloride and Related Combinations on Aerobic Plate Count and the Sensory Characteristics of Rainbow Trout," *Lebensm.-Wiss. u.-Technol.*, 31(3):286-290 (1998).

Odds et al., "Synergy, Antagonism, and What the Chequerboard Puts Between Them," The Journal of Antimicrobial Chemotherapy, 52(1):1 (2003).

Rodriguez et al., "Pediocin PA-1, a Wide-Spectrum Bacteriocin from Lactic Acid Bacteria," *Critical Reviews in Food Science and Nutrition*, 42(2):91-121 (2002).

Schlyter et al., "The Effects of Diacetate with Nitrite, Lactate, or Pediocin on the Viability of *Listeria monocytogenes* in Turkey Slurries," *International Journal of Food Microbiology*, 19(4):271-281 (1993).

Tagg et al., "Bacteriocins of Gram-Positive Bacteria," *Bacteriol. Rev.*, 40:722-756 (1976).

Turcotte et al., "A Rapid Turbidometric Microplate Bioassay for Accurate Quantification of Lactic Acid Bacteria Bacteriocins," *Int. J. Food Microbiol.*, 90(3):283-293 (2004).

Ukuku et al., "Use of Hydrogen Peroxide in Combination with Nisin, Sodium Lactate and Citric Acid for Reducing Transfer of Bacterial Pathogens from Whole Melon Surfaces to Fresh-Cut Pieces," *International Journal of Food Microbiology*, 104:225-233 (2005).

Vollenweider et al., "3-Hydroxypropionaldehyde: Applications and Perspectives of Biotechnological Production," *Appl. Microbiol. Biotechnol.*, 64(1):16-27 (2004).

International Search Report and Written Opinion for Application No. PCT/CA2013/050290, dated Jul. 18, 2013.

Degnan et al., "Use of Pediococcus-Acidilactici to Control Listeria-Monocytogenes in Temperature-Abused Vacuum-Packaged Wieners," *Journal of Food Protection, International Association for Food Protection*, vol. 55, No. 2, pp. 98-103 (1992).

El-Khateib et al., "Inactivation and attachment of Listeria monocytogens on beef muscle treated with lactic acid and selected bacteriocins," *Journal of Food Protection, International Association for Food Protection* vol. 56 No. 1, pp. 29-33 (1993).

Kim Soon Yeon et al., "Syngergistic effect of citric acid and pediocin K1, a bacteriocin produced by *Pediococcus* sp. K1, on inhibition of Listeria monocytogenes," *Journal of Microbiology and Biotechnology*, vol. 11, No. 5, pp. 831-837 (2001).

(56) References Cited

OTHER PUBLICATIONS

European Search Report for Application No. 13778929.3, dated Nov. 25, 2015.

* cited by examiner

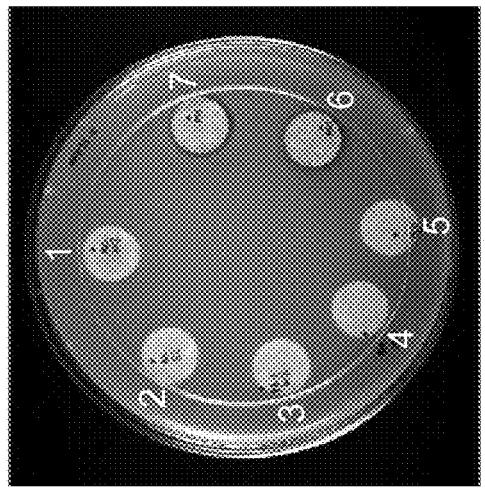
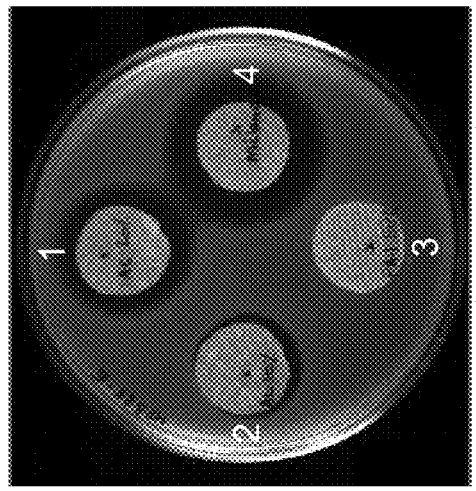
FIG. 6A
1: Acetic acid (10%)
2: Lactic acid (5%)
3: Pediocin PA-1 (4000AU/ml)
4: Reuterin (128 AU/ml)
5: Distilled water
6: Mix II
7: Mix I
FIG. 6B
1: Acetic acid (20%)
2: Lactic acid (10%)
3: Pediocin PA-1 (4000AU/ml)
4: Mix II

ANTIMICROBIAL COMPOSITIONS AND USES THEREOF

The present invention relates to antimicrobial compositions, and more particularly to antimicrobial compositions having bactericidal activity, uses and methods thereof.

Emerging infectious diseases are becoming more devastating even in developed countries where sanitary conditions are often very rigorous. These diseases are now not only a major threat to the population but also a great challenge for the health sector authorities. The large diversity of source contamination, the emergence and rapid spread of multidrug resistant microorganisms as well as the involvement of many transmission vectors of these pathogens are important factors that cause these diseases to spread quickly before effective control measures can be implemented.

One of the strategies used to reduce the impact of these emerging diseases is the development of programs to stop the transmission cycle of pathogenic microorganisms in different target areas. Thus various programs of cleaning and disinfection in health as well as in food industries have been recently implemented.

To prevent or slow the spread of microorganisms in health and food industries, a wide variety of products such as antimicrobial soap, spray, liquid, liquid surface and wipes have been developed.

Bacteriocins and organic acids have been used to control the growth of microorganisms mostly in food. Bacteriocins are low-molecular-weight proteins which inhibit the growth of similar or closely related bacterial strain(s) (Ennahar, 2000). A data base comprising most of the well characterized bacteriocins as well as their respective characteristics has recently been developed by Hammami et al. 2009. One of the most studied bacteriocin is Nisin which is the only bacteriocin generally recognized as safe (GRAS) by the American Food and Drug Administration. It is currently used as additive/preservative in different food matrices such as in milk (Benech et al. 2002) meat based products (Abee et al. 1995, Cutter, 2001), marine products (Nilsson et al. 2002) and plant products (Allende et al. 2007).

U.S. Pat. No. 5,573,800 relates to an antimicrobial product comprising a pediococcus-derived bacteriocin or synthetic equivalent antimicrobial agent in combination with a chelating agent reported as having anti-*Listeria monocytogenes* activity and used as a food preservative.

EP application 2 289 350 relates to dough compositions containing natural antimicrobial agent to preserve the dough. The latter can contain both encapsulated organic and natural antimicrobial agent.

WO 2005/104878 relates to an antimicrobial composition comprising an antimicrobial material, an organic acid and an emulsifier.

The present description relates to compositions, uses and methods thereof.

In one aspect the composition is:
a) a composition comprising at least two organic acids selected from the group consisting of lactic acid, acetic acid, benzoic acid and citric acid;
b) a composition comprising at least two bacteriocin selected from the group consisting of pediocin, Nisin and reuterin;
c) a composition comprising pediocin and at least two organic acids selected from the group consisting of lactic acid, acetic acid, benzoic acid and citric acid; or
d) a composition comprising reuterin and at least one organic acid selected from the group consisting of lactic acid, acetic acid, benzoic acid and citric acid.

In one aspect, the compositions have synergistic activity.
In one aspect, the compositions are stable.
In one aspect, the compositions have an antimicrobial activity against Gram-positive and Gram-negative bacteria.
In one aspect, there is provided a use of the antimicrobial composition as defined herein for sanitizing and/or disinfecting a surface.
In one aspect, there is provided a cellulosic substrate comprising the antimicrobial composition as defined herein.
In one aspect, there is provided a use of the cellulosic substrate as defined herein for sanitizing and/or disinfecting a surface.
In one aspect, there is provided a food packaging comprising the antimicrobial composition as defined herein.
In one aspect, there is provided a use of the food packaging as defined herein as an active food packaging.
In one aspect, there is provided a method for sanitizing and/or disinfecting a surface, comprising applying an effective antimicrobial amount of the antimicrobial composition as defined herein to the surface.

Figure 5:
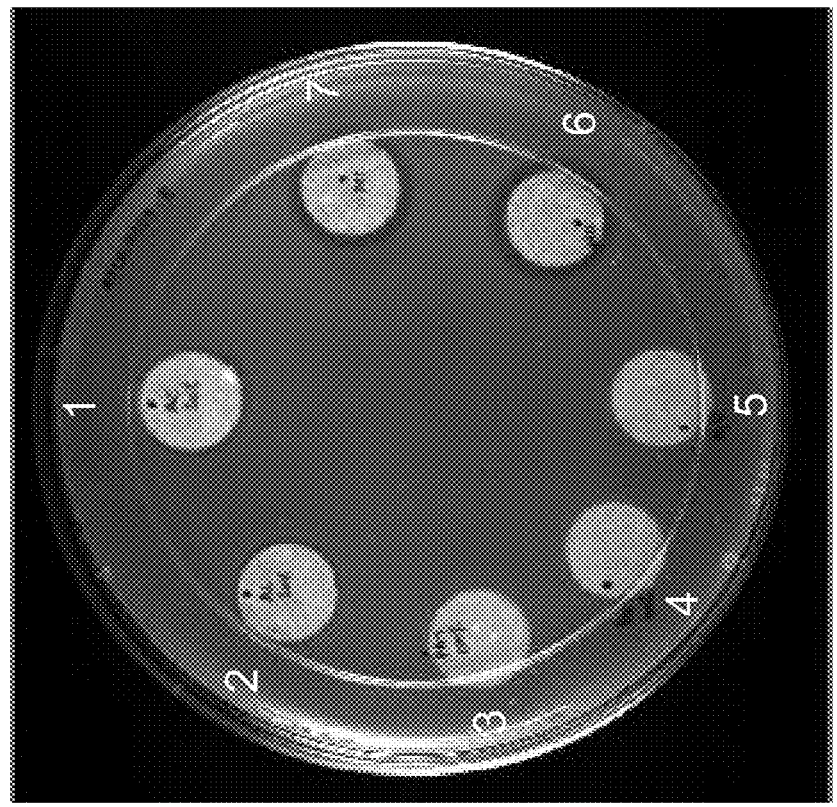
Figure 9:
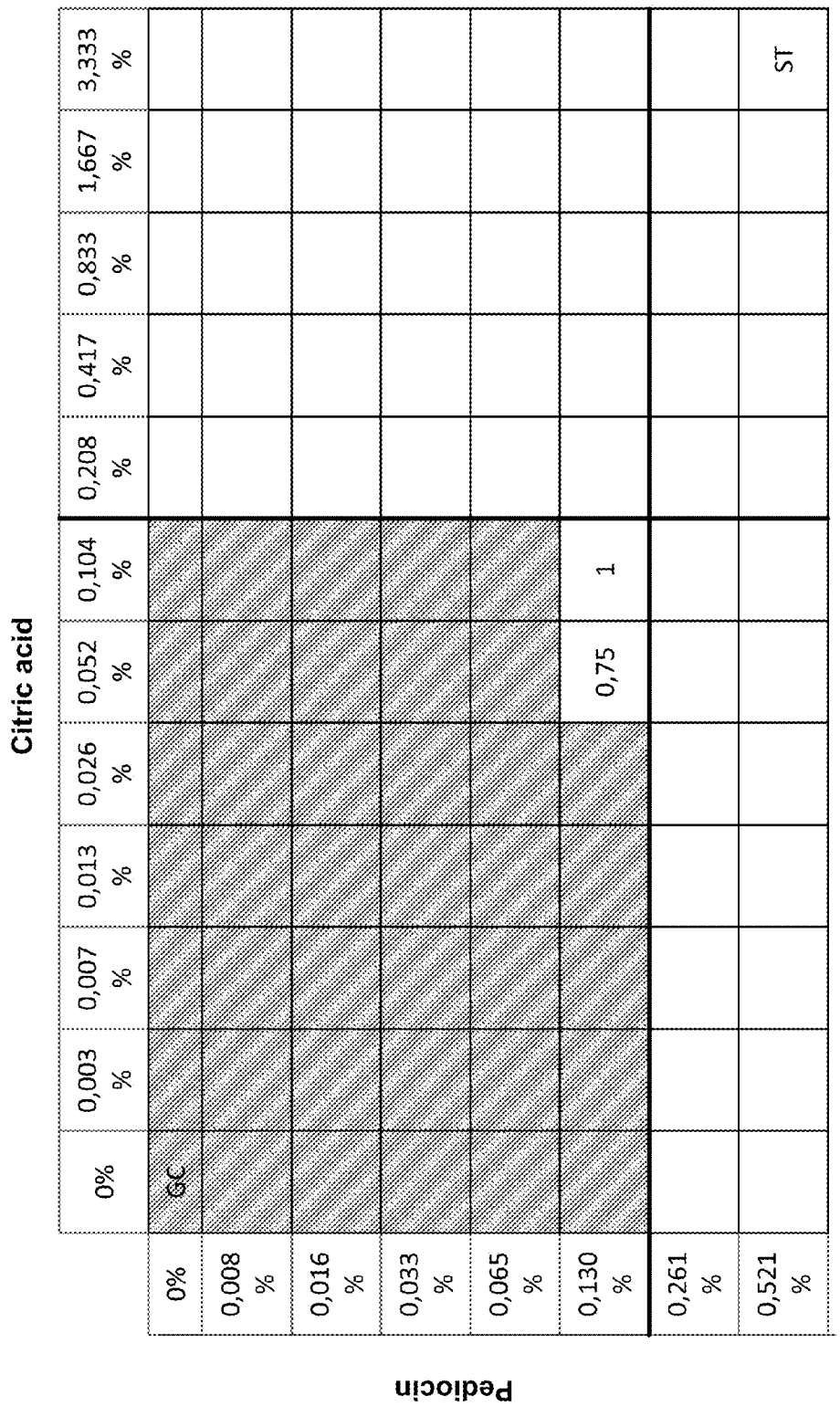
Figure 10:
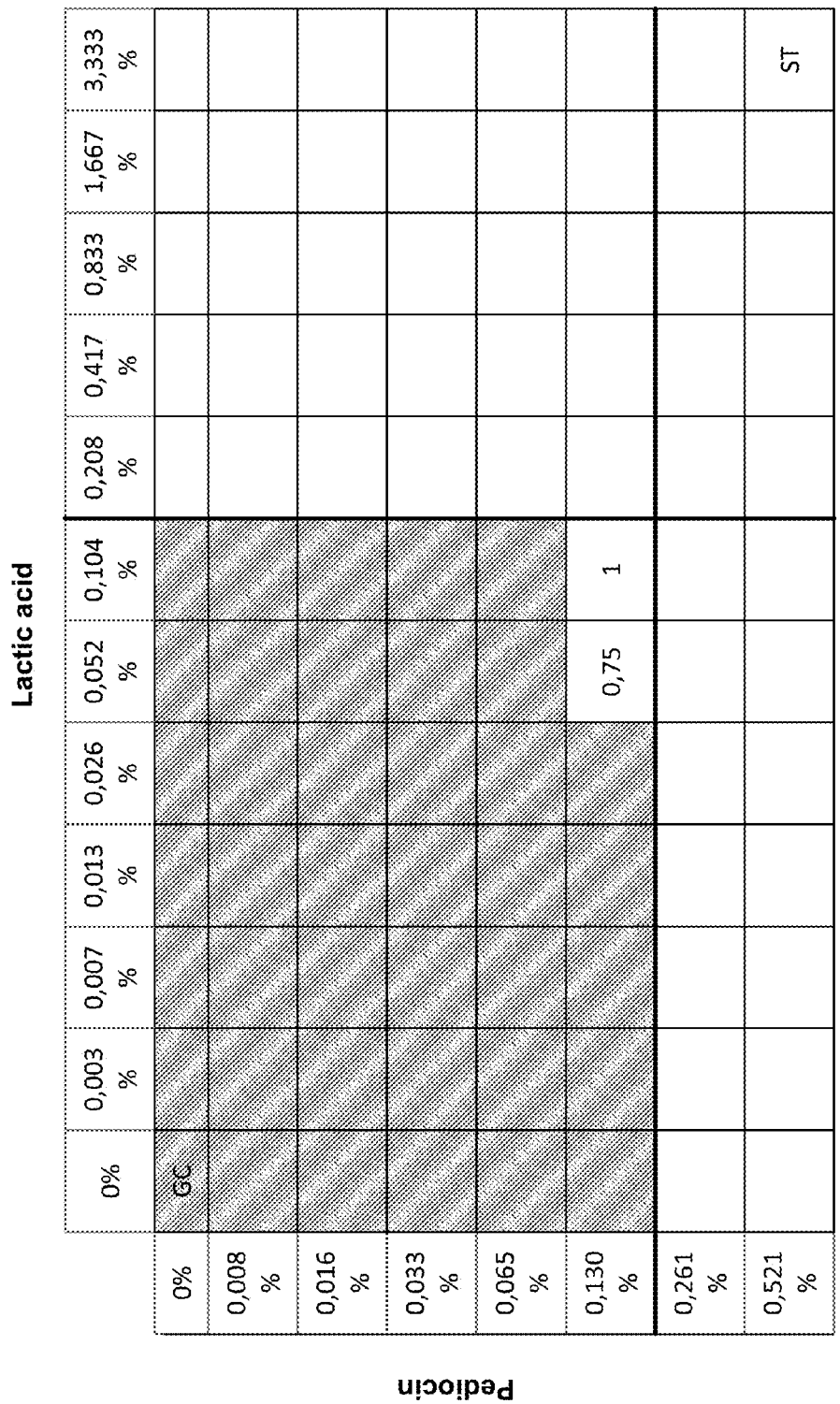
Figure 11:
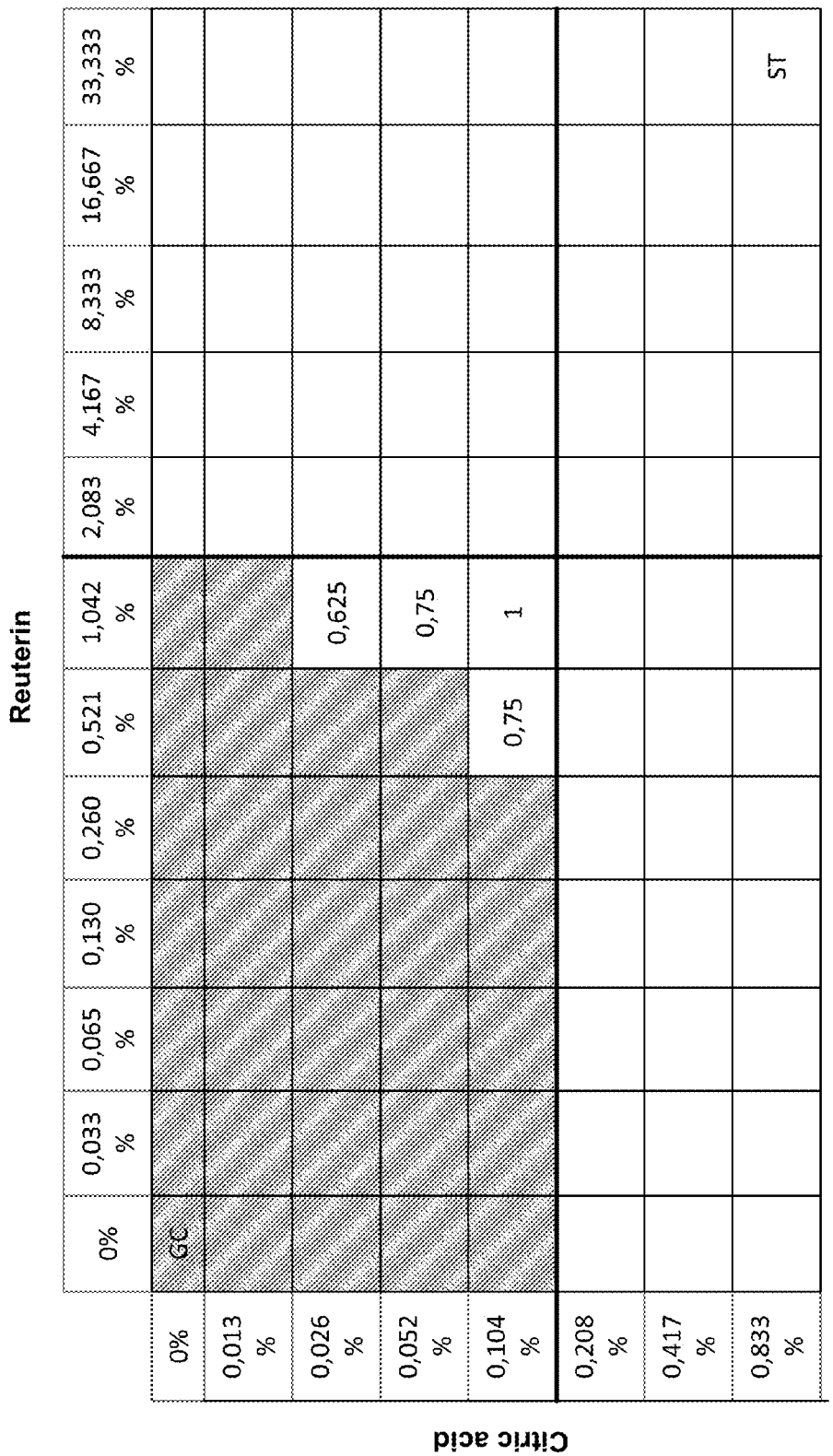
Figure 12:
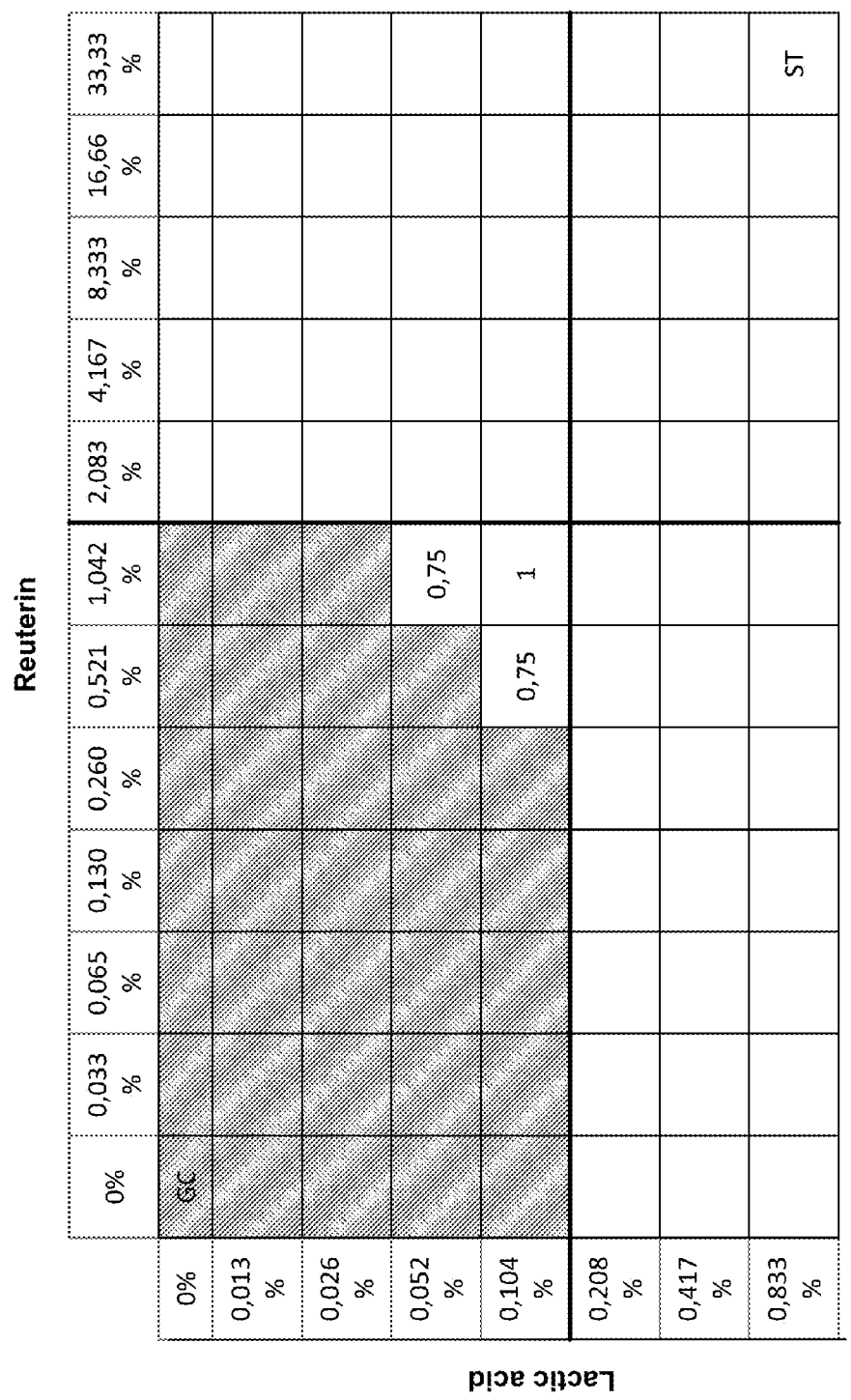
Figure 13:
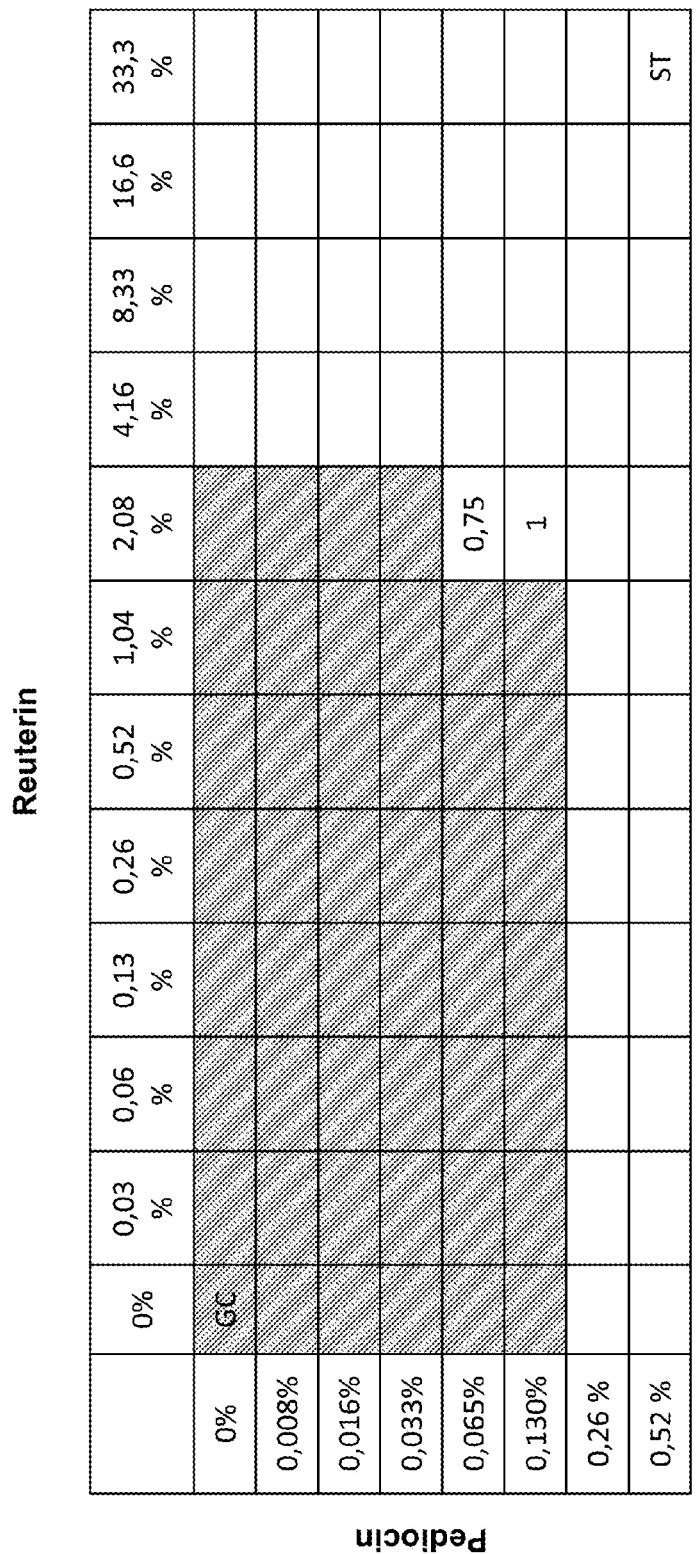
Figure 14:
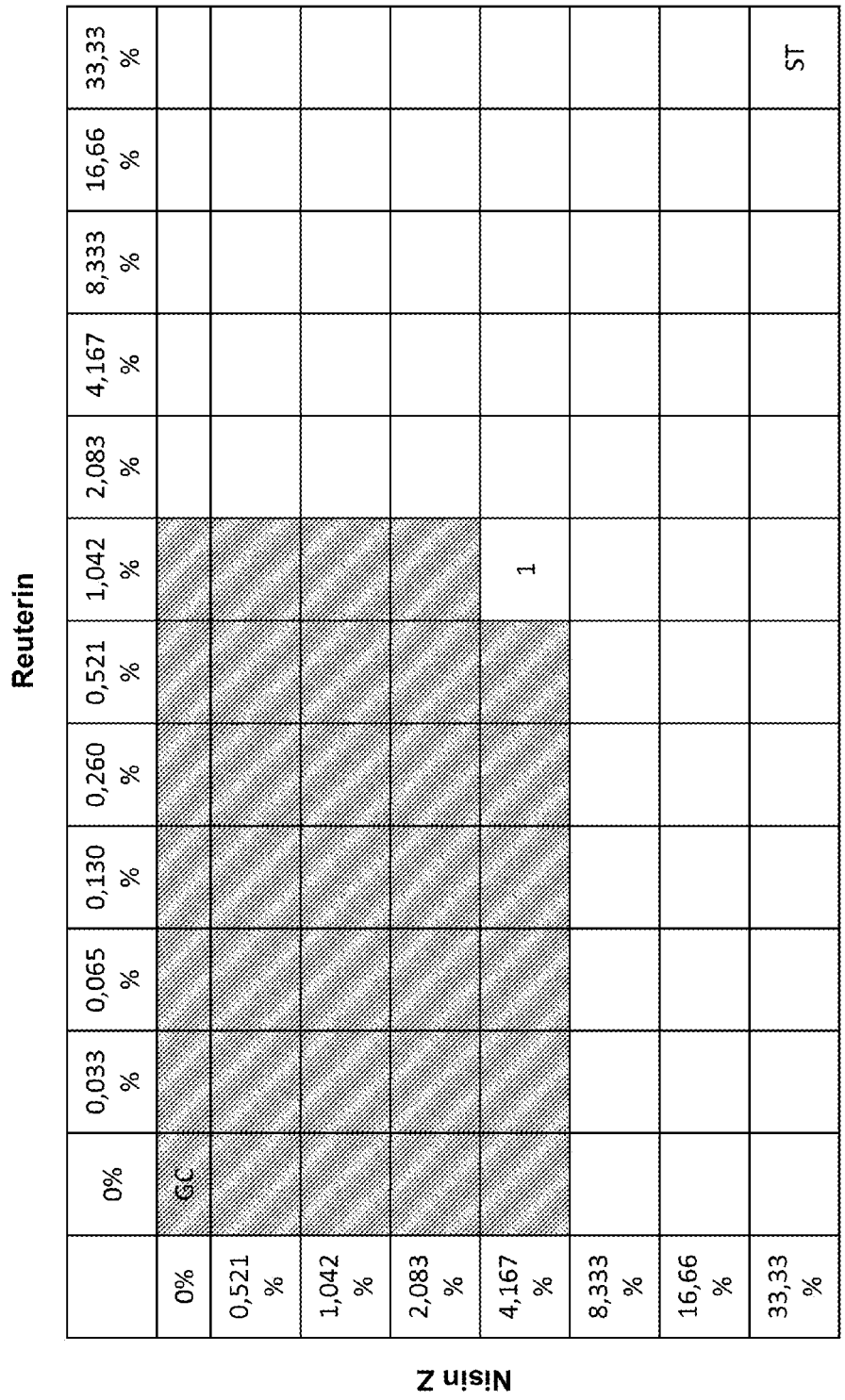

FIG. 1: Inhibition activity of Mix II against *E. coli* ATCC 11229 (A) and *Listeria. ivanovii* HPB28 (B) determined by the microplate microdilution method;

FIG. 2: Inhibition activity of Mix I against *E. coli* ATCC 11229 (A) and *Listeria ivanovii* HPB28 (B) determined by the microplate microdilution method;

FIG. 3: Log reduction of *E. coli* ATCC 11229 obtained with Mix I (A) and II (B) after different contact time using the AOC 960.0 method;

FIG. 4: Log reduction of *S. aureus* ATCC 6538 obtained with Mix I (A) and II (B) after different contact time using the AOC 960.0 method;

FIG. 5: Inhibition activity against *E. coli* ATCC 11229 of towel paper soaked in Mix I and II determined by the agar diffusion test;

FIG. 6: Inhibition activity against *Listeria ivanovii* HPB of towel paper soaked in Mix I and II (A) and Mix II (B) determined by the agar diffusion test;

FIG. 7: Inhibition activity against *E. coli* ATCC 11229 of Mix I (A) and II (B) determined by the microplate microdilution method;

FIG. 8: Inhibition activity against *Listeria ivanovii* HPB28 of Mix I (A) and II (B) determined by the microplate microdilution method;

FIG. 9. Interaction between citric acid and pediocin on *Listeria*. (FIC index);

FIG. 10. Interaction between lactic acid and pediocin on *Listeria*. (FIC index);

FIG. 11. Interaction between reuterin and citric acid on *Listeria*. (FIC index);

FIG. 12. Interaction between reuterin and lactic acid on *Listeria*. (FIC index);

FIG. 13. Interaction between reuterin and pediocin on *Listeria*. (FIC index); and FIG. 14. Interaction between reuterin and nisin Z on *Listeria* (FIC index).

In one aspect, the compositions have a synergistic antimicrobial activity. In a further aspect, the compositions have a large-spectrum antimicrobial activity. In a further aspect, the compositions have a synergistic large-spectrum of antimicrobial activity. In a further aspect, the compositions could be used on a wide variety of surfaces. In a further aspect, the compositions could be used for sanitation and/or disinfection of surfaces. In one aspect the compositions could be used without any rinsing step.

The term "synergistic" as used herein refers to the effect obtained by combining compounds and/or agent which is greater than the effect obtained by the separate addition of each compound. Methods for determining the potential synergistic effect of combinations are known. Synergistic activity could be determined using the Fractional Inhibitory Concentration (FIC) index by the broth microdilution method. According to this method, a combination having a FIC index <0.5 is considered as synergistic, a combination having 0.5<FIC index ≤1 is considered as moderate synergistic, a combination having a 1.0<FIC index ≤4.0 is considered as indifferent and a combination having a FIC index >4 is considered an antagonist. In one aspect, the compositions have a moderate or a high synergic effect as determined by the FIC method. In a further aspect, the compounds could be combined at lower than their MICs. In one aspect, the compositions having a synergistic effect allow the use of lower concentration of each compound or agent.

The expression "percentage by weight or volume" refers to the mass or the volume of one substance relative to the mass or the volume of the total mixture mass or mixture volume. These amounts are calculated assuming equal weight for equal volumes.

The term "AU/ml" refers to arbitrary units per ml. Methods for evaluating the AU/ml of bacteriocins are known such as described in Turcotte et al. 2004.

The terms "antimicrobial composition" or "antimicrobial activity" as used herein refer to inhibition and/or reduction of the growth of microorganisms including multicellular, unicellular or acellular organisms such as bacteria, fungi, yeast, mold, archea, protists, virus, algae, plankton and planarian. Methods for evaluating the antimicrobial activity of a composition are known such as agar diffusion test, agar and broth dilution methods, Stokes method, E-test. The activity can also be measured by calculating the log reduction in number of microorganisms.

In one aspect, the compositions have antimicrobial activity against gram positive and gram negative bacteria. In a further aspect, the compositions have synergistic activity against gram positive and gram negative bacteria.

The compositions as described herein could be used for sanitizing and/or disinfecting surfaces. The terms "sanitation" or "sanitizing" refer to a 1 to 3-log reduction in number of microorganisms on the surfaces to be treated. In one embodiment, the term "sanitation" refers to a 3-log reduction in number of microorganisms on the surfaces to be treated. The term "disinfectant" refers to a 3 to 5-log reduction in number of microorganisms on the surfaces to be treated. In one embodiment, the term "disinfecting" refers to a 5-log reduction in number of microorganisms on the surfaces to be treated. Methods for determination of log reduction in number of microorganism are well known such as the film contact method, or the AOAC 960.09 method (AOAC Official Methods of Analysis (2000), Disinfectants, chapter 6, p. 10).

The expression "Gram-positive" refers to bacteria that are stained dark blue or violet by Gram staining as opposed to Gram-negative bacteria which can not retain the violet stain. Gram-positive bacteria are able to retain the crystal violet strain because of the high amount of peptidoglycan in their cell wall. Gram-positive cell wall typically lack the outer membrane found in Gram-negative bacteria. Gram-positive bacteria are known such as *Enterococcus faecium, Staphylococcus aureus, Listeria monocytogenes* Scott 3, *Corynebacterium, Streptococcus* M3, *Streptococcus agalactiae, Streptococcus* sp, *Clostridium difficile* and so on.

The expression "Gram-negative" refers to bacteria that do not retain the crystal violet dye in the Gram staining protocol. In the Gram stain test, a couterstain is added after the crystal violet coloring the Gram-negative bacteria with a red or pink color. Gram-negative bacteria are known such as *Aeromonas, Escherichia coli* O157:H7, *Escheria coli, Pseudomonas fluorescens, Serratia marcescens, Salmonella* sp, *Pseudomonas aeroginosa, Aeromonas Hydrophila, Pseudomonas euroginosa, Erwinia, Yersinia enterocolitica* and so on.

The expression "organic acid" refers to an organic compound with acidic properties. The most common organic acids are the carboxylic acids whose activity is associated with their carboxyl group-COOH such as lactic acid, acetic acid and citric acid. Several organic acids are naturally produced by strains of lactic acid bacteria such as those belonging to the genus *lactococcus, lactobacillus* and *pediococcus*.

The term "citric acid" refers to a weak organic acid ($C_2H_4O_2$) that could exist in an anhydrous or as a monohydrate form. This term also refers to the conjugate base of citric acid ($C_2H_6O(COO)_3^{3-}$) or to the esters of citric acid. Citric acid could be produced by culturing bacteria such as *A. niger* fed on a sucrose or glucose-containing medium. As such, citric acid, the conjugate base and the esters could be purchased.

The term "lactic acid" refers to a carboxylic acid ($C_3H_6O_3$) having a hydroxyl group adjacent to the carboxyl group, making it an alpha hydroxyl acid (AHA). This term also refers to the conjugate base of lactic acid or to the esters of lactic acid. Lactic acid could be obtained by lactic acid fermentation performed by lactic acid bacteria. Lactic acid, the conjugate base and the esters could be purchased.

The term "benzoic acid" refers to an organic acid ($C_7H_6O_2$), to its conjugate base or to its acid known as benzoates. Benzoic acid could be produced commercially.

The term "bacteriocin" as used herein refers to proteinaceous toxins of low molecular weight that could be produced by bacteria such as Lactic acid bacteria to inhibit the growth of similar or closely related bacterial strain(s). Bacteriocins could typically be isolated from a broth into which bacteria have grown or they could be chemically synthesized.

The term "pediocin" includes class IIa or pediocin-like bacteriocins that could be produced by lactic acid bacteria. Class II bacteriocins are a class of small peptides that inhibits the growth of various bacteria. Lactic acid bacteria such as *Pediococcus acidilactici, Pediococcus parvulus* and *Lactobacillus plantarum* secrete pediocin PA-1, AcH or SJ-1 which kill target cells by permeabilizing the cell membrane (Ennahar S. et al. Class IIa bacteriocins: biosynthesis, structure and activity. FEMS Microbiology Reviews, 24, 2000, p. 85-100). The nucleic acid sequences as well as the amino acid sequences of pediocin PA-1, AcH and SJ-1 are known. (Gene bank, Nucleic Acids Research, 2011 January 39 (database issue) D32-7). In a further embodiment, the compositions described herein comprise pediocin PA-1. Pediocin could be isolated from a bacteria culture broth such as *Pediococcus acidilactici* culture grown in MRS broth overnight or could be chemically synthesised. Pediocin bacteriocin activity could be assayed by agar diffusion test.

The term "Nisin" includes a lanthione-containing bacteriocin having a polycyclic peptide with 34 amino acid residues. In one aspect, the Nisin contains the amino acids lanthionine, methyllanthionine, dehydroalanine and dehydro-amino-butyric acid. Nisin could be obtained by fermentation using bacterium *Lactococcus lactis*. Nisin could also be chemically synthesized. Nisin is also available commercially. In one embodiment, Nisin is Nisn A or Nisin Z. Nisin having a histidine at position 27 is referred as "Nisin A" and Nisin having an asparagine at position 27 is referred as "Nisin Z". The nucleic acid sequences as well as the amino acid sequences of Nisin, Nisin A and Nisin Z are known.

In one embodiment, Nisin, Nisin A and Nisin Z include a nucleic acid or an amino acid sequence at least 65% to 95% identical, at least 65%, 70%, 75%, 80%, 85%, 90% identical or at least 95% identical to part or all of the nucleic acid or amino acid sequence of Nisin, Nisin A or Nisin Z, respectively.

In one embodiment, pediocin includes a nucleic acid or an amino acid sequence at least 65% to 95% identical, at least 65%, 70%, 75%, 80%, 85%, 90% identical or at least 95% identical to part or all of the nucleic acid or amino acid sequence of pediocin PA-1, AcH or SJ-1.

Techniques for determining nucleic acid and amino acid "sequence identity" are also known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) could be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm could be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). Another method of establishing percent identity which could be used in the context of the present description is the MPSRCH package of programs copyrighted by the University of Edinburgh, developed by John F. Collins and Shane S. Sturrok, and distributed by Intelli-Genetics, Inc. (Mountain View, Calif.). From this suite of packages the Smith-Waterman algorithm could be employed where default parameters are used for the scoring table (for example, gap open penalty of 12, gap extension penalty of one, and a gap of six). From the data generated the "Match" value reflects "sequence identity." Other suitable programs for calculating the percent identity between sequences are generally known in the art, for example, another alignment program is BLAST, used with default parameters. For example, BLASTN and BLASTP could be used using the following default parameters: genetic code=standard; filter=none; strand=both; cutoff=60; expect=10; Matrix BLOSUM62; Descriptions=50 sequences; sort by=HIGH SCORE; Databases=non-redundant, GenBank+EMBL+DDBJ+PDB+GenBank CDS translations+Swiss protein+Spupdate+PIR.

The term "reuterin" includes a multi-compound that could be produced by *Lactobacillus reuteri* during the metabolism of glycerol to 1,3-propanediol. Reuterin typically consists of 3-hydroxypropionaldehyde and is in a dimer form in dynamic equilibrium. Without being bound to a specific theory, the mechanism of action of reuterin could involve a competition with ribonucleotides for binding to the ribose recognition site of ribonucleotide reductase which is the first enzyme involved in DNA synthesis. Reuterin seems to inhibit the conversion of ribonucleotides into deoxyribonucleotides and hence exert its antimicrobial effect (Vollenweider S, Lacroix C: Appl Microbiol Biotechnol 2004).

Reuterin could be chemically synthesized. In one aspect, reuterin could also be isolated from bacteria culture broth. In one aspect, reuterin could be extracted from *Lactobacillus reuteri* ATCC 53608 culture grown in MRS broth overnight. Reuterin bacteriocin activity could be assayed by the agar diffusion test described herein.

The term "about" is intended to represent a variation of ±10% of the values provided herein.

In one aspect, there is provided a cellulosic substrate comprising the compositions as defined herein. The expression "cellulosic substrate" refers to a thin material produced by pressing together moist fibers, typically cellulose pulp derived from wood, rags or grasses and drying into flexible sheets. The cellulosic substrate could also be produced from recycled material such as recycled paper. Examples of cellulosic substrate are hygienic paper, facial paper, cardboard, paper towels, wrapping paper, toilet paper or table napkin, moulded pulp and the like.

The antimicrobial activity of the compositions as described herein on a cellulosic substrate could be determined by soaking the cellulosic substrate in the compositions to be tested and plating the cellulosic substrate on agar. An agar diffusion test could then be performed.

The compositions could therefore be applied on a cellulosic substrate prior to sanitizing and/or disinfecting surfaces. The cellulosic substrate soaked with the compositions could be used for sanitizing and/or disinfecting surfaces.

The term "surface" refers to the outer of the topmost boundary of an object to be treated. In one embodiment, the surface to be treated could be located in health care facilities, food plants, spas, exercise facilities and the like. In one embodiment, the surface to be treated is food, food packaging, counter top, desk, floor, wall, sauna, pool, and the like. The term "surface" may also comprise a body parts such as hands, feet, arms, legs and the like. The compositions as described herein could be used for sanitizing and/or disinfecting the surface as described above, thus reducing the number of microorganisms on said surface. For instance, the compositions as described herein could be used to sanitizing and/or disinfecting kitchen countertop on which food is manipulated. The compositions as described herein could also be used to sanitizing and/or disinfecting food packaging. The compositions as described herein could also be used for sanitizing and/or disinfecting hands. In one aspect, the compositions could be used without rinsing step. In a further aspect, the compositions could be used safely on various surfaces as well as on food.

In another embodiment, the food packaging could comprise the antimicrobial composition described herein. In one embodiment, the antimicrobial composition described herein is applied, coated, vaporized or immobilized on the food packaging. In one embodiment, the food packaging comprising the antimicrobial composition described herein is an active food packaging. The active food packaging comprising the antimicrobial composition described herein could inhibit and/or reduce the growth of microorganisms and as such be used to maintain and/or enhance food quality, food sensory properties, food safety and/or food shelf-life.

The term "objects" refers to something material that may be perceived by the senses such as toy, dishes, telephone and the like. As such, the compositions could be used to sanitize and/or disinfect any objects.

The term "food" refers to a material usually from a plant or animal origin that contains or consists of essential body nutrients produced for animal or human consumption. Examples of food that could be sanitized and/or disinfected with the compositions described herein are fruits, vegetables, meat, and fishes. In one aspect, the compositions could be safely used on food.

The expression "body part" refers to any part of a human or an animal that is part of the body, such as hands, face, feet, arms, legs, neck, head or torso. The compositions as described herein could be used as hands sanitizer in order to sanitized and/or disinfected hands.

The expression "food plant" refers to a location where food is processed, packed, or shipped. The surfaces of the food plant such as counter tops, wall, floor could thus be sanitized and/or disinfected with the compositions as described herein.

The expression "food packaging" refers to a material used for packing food. In one embodiment, the food packaging could be a film, resin, liner, absorbent pad, plastic, shrink bag, shrink wrap, plastic wrap, Styrofoam, carton, cellulosic substrate and the like.

In one aspect, the compositions as described herein are stable e.g. their activity does not significantly decrease over a predetermined period of time. In one aspect, the shelf life of these compositions is stable for the intended use. In another aspect, this synergistic activity is stable for several days at both 4 and 25° C. In a further aspect, the synergistic activity is stable for 60 days.

In another aspect there is provided, a method for sanitizing and/or disinfecting a surface. The method comprises applying an effective antimicrobial amount of antimicrobial composition as defined herein to the surface. The expression "effective antimicrobial amount" refers to an amount of the antimicrobial composition applied to the surface sufficient to obtain at least 1-log reduction in number of microorganisms on the surface.

The compositions as described herein may further comprise surfactants. The term "surfactant" refers to a type of molecule which has both hydrophobic and hydrophilic portions, which allows it to stabilize and disperse hydrophobic molecules and aggregates of hydrophobic molecules in aqueous systems. As such, the surfactant is capable of dispersing components of the compositions as described herein in an aqueous solution. Suitable surfactant could be monoglycerides, diglycerides, sucrose or fatty acid esters.

The compositions as described herein could also include stabilizing agents, wetting agents, as well as pigments or dyes among any number of constituents which could be added to the compositions without substantially affecting the antimicrobial activity or the stability of the compositions. Stabilizing agents refer to chemical that inhibits separation of suspensions, emulsions and foams. Wetting agents increase the spreading and penetrating properties of a liquid by lowering its surface tension. Pigments or dyes change the color of reflected or transmitted light as the result of wavelength-selective absorption. Suitable agents, dyes or pigments that could be added without affecting the antimicrobial activity or the stability of the compositions described herein are known.

The compositions described herein could be in form of gel, foam, ointment, liquid, spray or powder. The term "gel" refers to a solid, jelly-like material that could have properties ranging from soft and weak to hard and tough. A gel is a substantially dilute cross-linked system, which exhibits no flow when in the steady-state.

The term "foam" refers to a substance that is formed by trapping pockets of gas in a liquid or a solid.

The term "ointment" refers to a homogenous, viscous, semi-solid preparation with a high viscosity that could be intended for external application such as to the skin or mucous membranes.

The term "liquid" refers to the composition having a definite volume but not a fixed shape. As such, acids, pediocin and reuterin could be solubilised or diluted in a liquid such as water and form a liquid.

The term "spray" refers to a dynamic collection of drops dispersed in a gas. The process of forming a spray is known as atomization. The compositions as described herein could thus be in a form of a spray.

The term "powder" refers to a dry, bulk solid composed of a large number of fine particles that may flow freely when shaken or tilted. The compositions described herein in form of powder could be solubilised in a liquid such as water before being used.

As shown at tables 1 and 2 a composition comprising citric acid and lactic acid has a FIC index of 0.75 on both *E. coli* ATCC 11229 and *Listeria ivanovii* HPB28 demonstrating a synergistic effect on both Gram-positive and Gram-negative bacteria. As also shown at tables 1 and 2 a composition comprising reuterin and pediocin have a FIC index of 0.75 on both *E. Coli* ATCC 11229 and *Listeria ivanovii* HPB28 demonstrating a synergistic effect on both Gram-positive and Gram-negative bacteria. Furthermore, tables 1 and 2 show that either lactic acid or citric acid in combination with either pediocin or reuterin has a synergistic effect (FIC index 1) on both *E. Coli* ATCC 11229 and *Listeria ivanovii* HPB28 demonstrating a synergistic effect on both Gram-positive and Gram-negative bacteria.

Figure 1B:
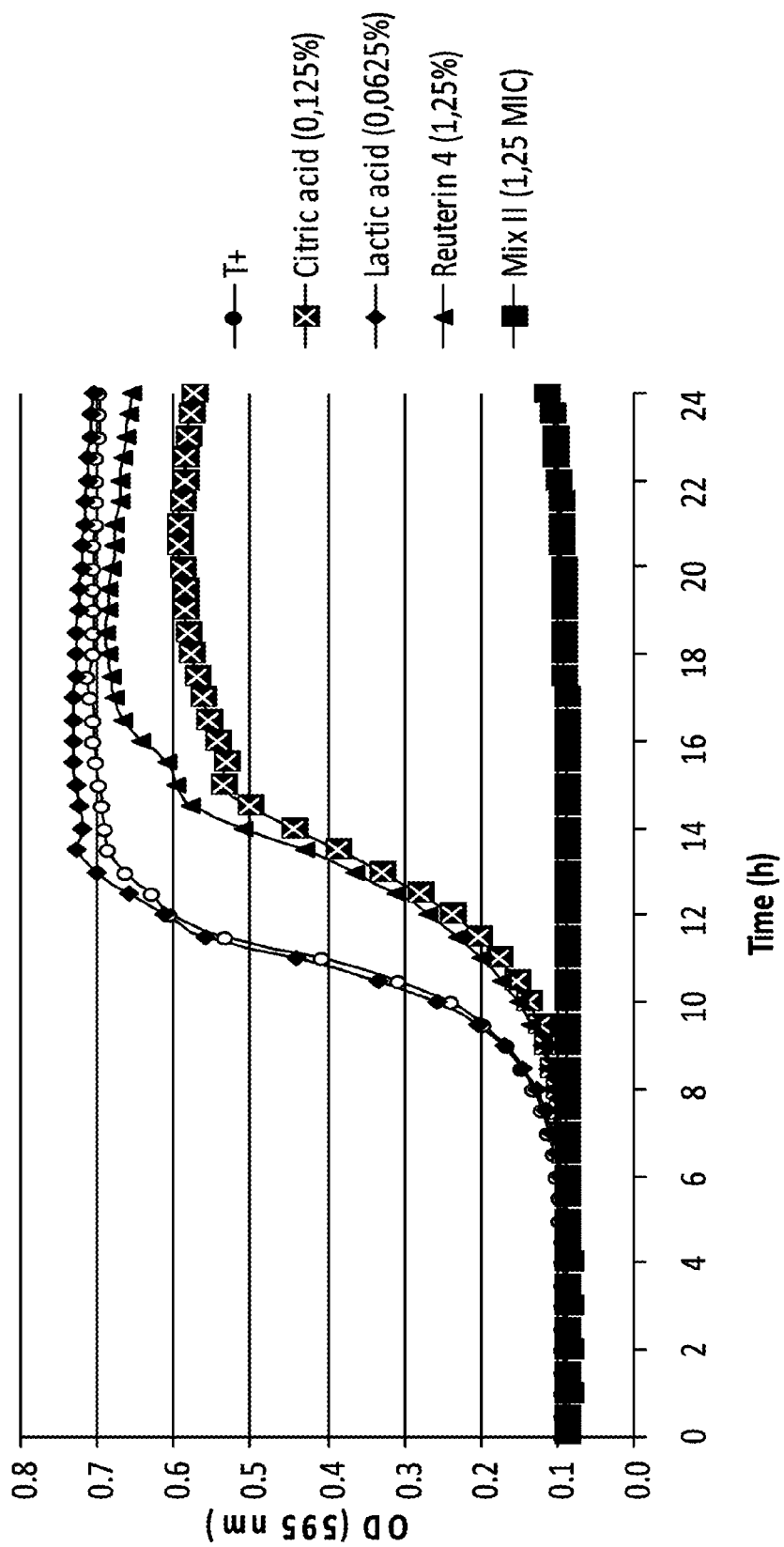
Figure 2A:
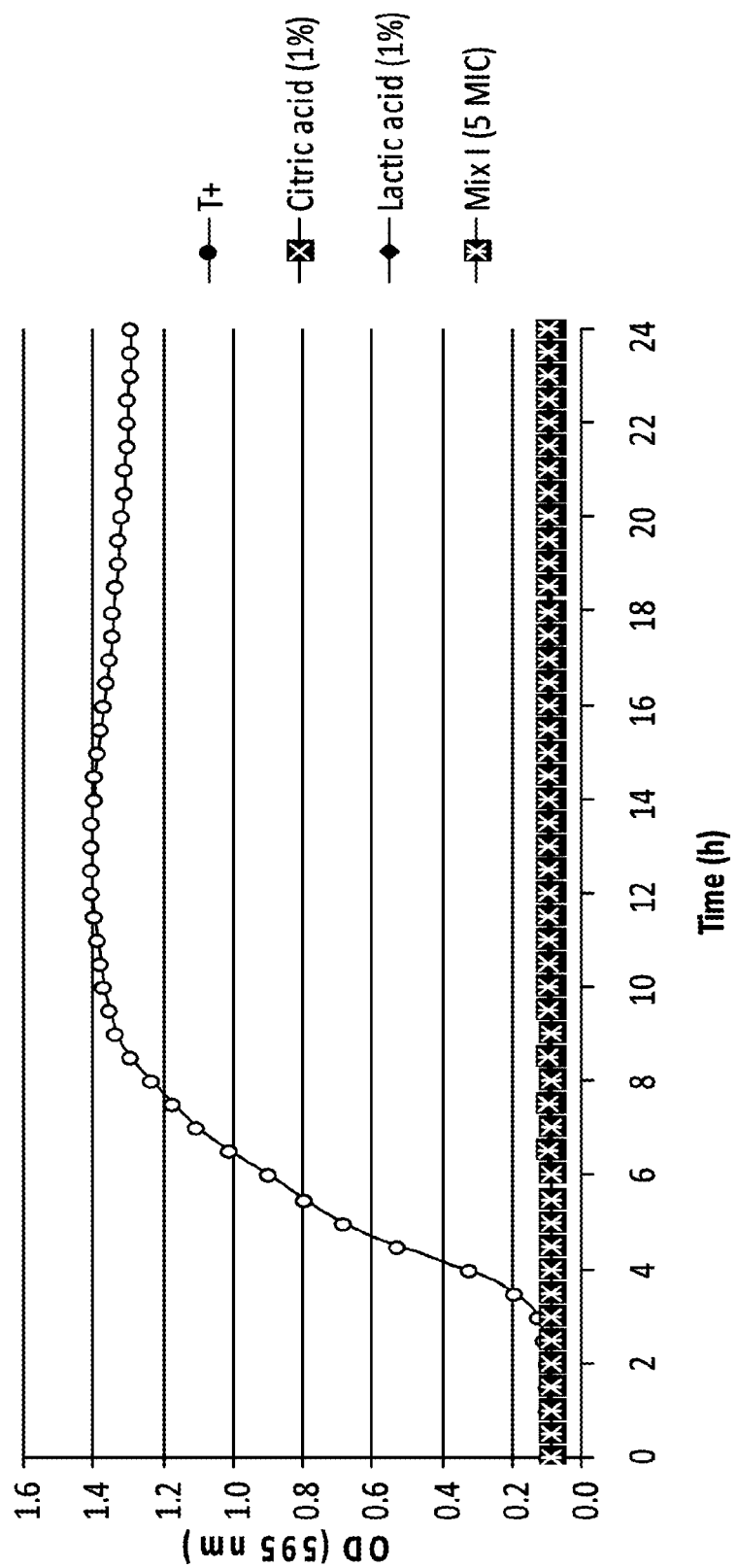
Figure 2B:
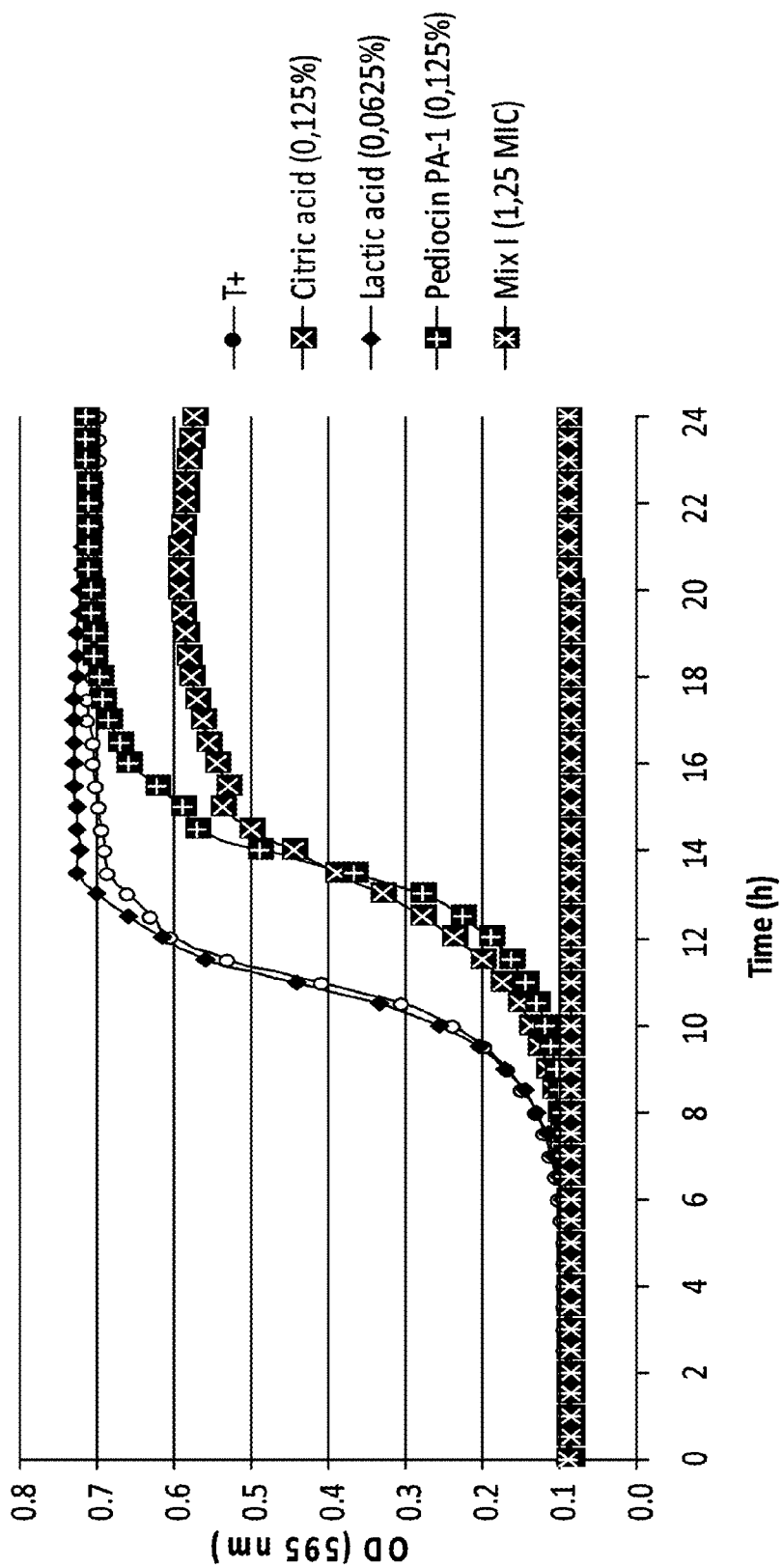

As further demonstrated at FIGS. 1A and 1B, lactic acid, citric acid and reuterin taken separately do not reduce the growth of *E. Coli* ATCC 11229 or *Listeria ivanovii* HPB28 as efficiently as when lactic acid, citric acid and reuterin are combined (Mix II). As shown at FIG. 2A, Mix I comprising citric acid (1%), lactic acid (1%) and pediocin inhibits the growth of *E. coli*. FIG. 2B shows that lactic acid (0.125%), citric acid (0.0625%) and pediocin taken separately do not reduce the growth of *Listeria ivanovii* HPB28 as efficiently as when lactic acid, citric acid and pediocin are combined (Mix I). The compositions could thus have a synergistic effect on the growth of both Gram-positive and Gram-negative bacteria.

Figure 3A:
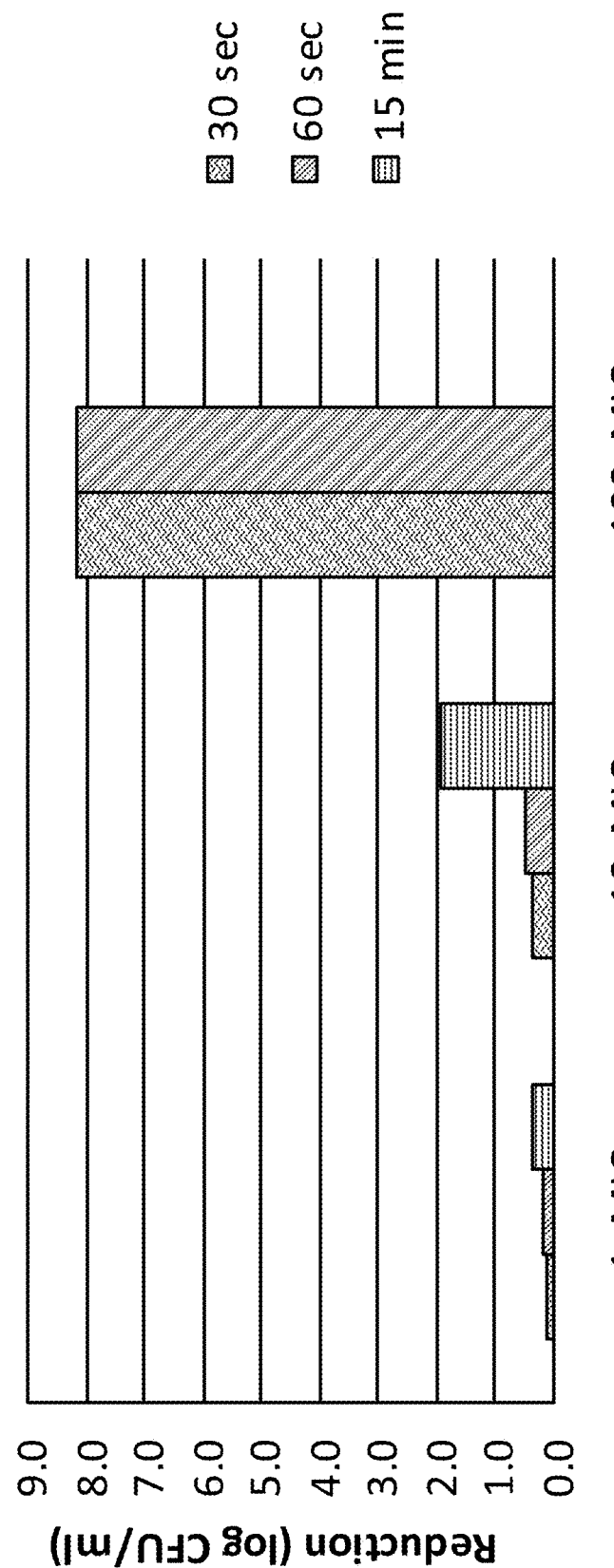
Figure 3B:
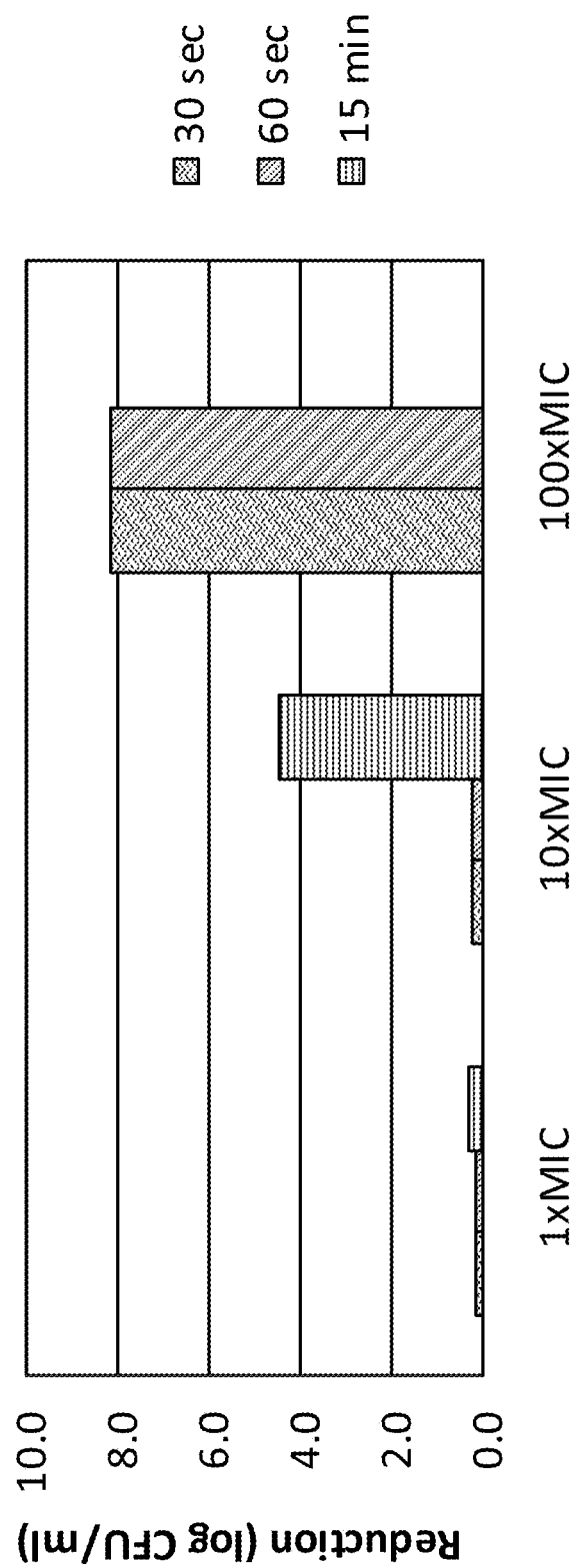
Figure 4A:
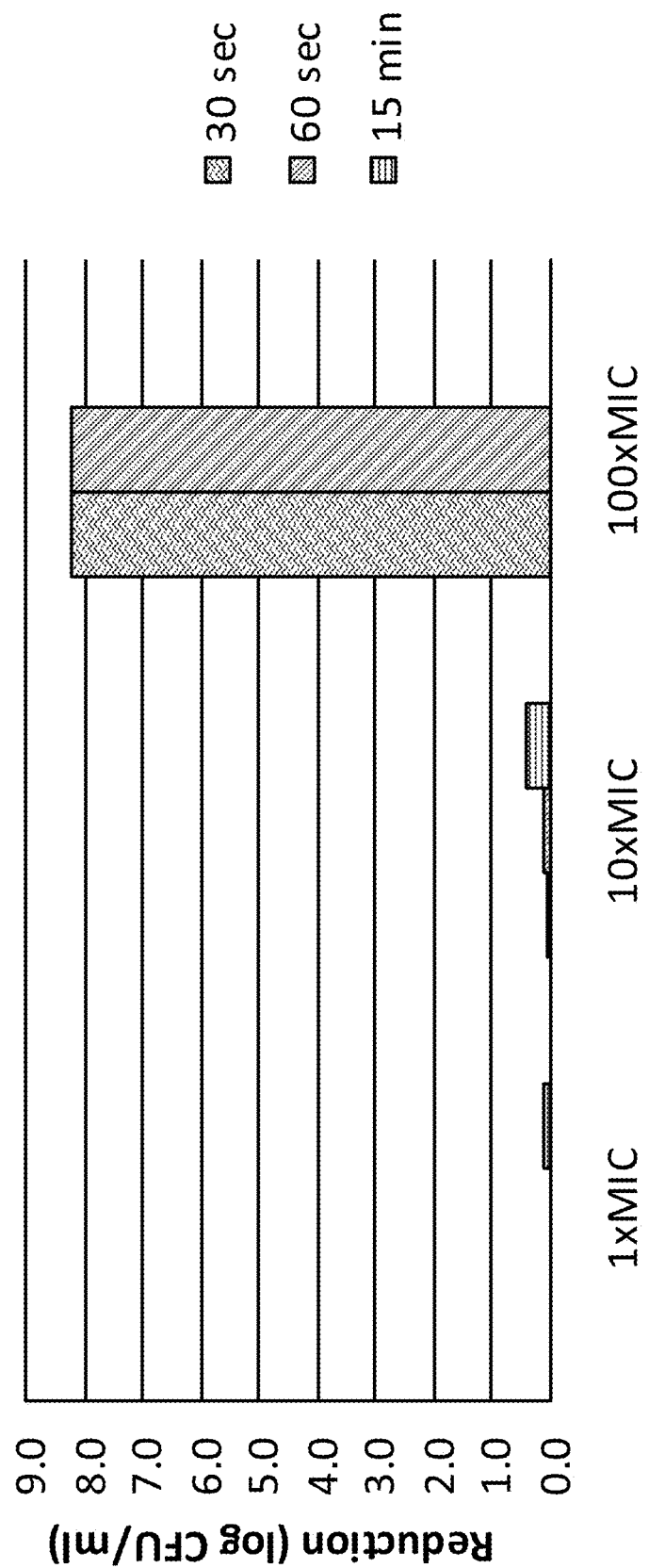
Figure 4B:
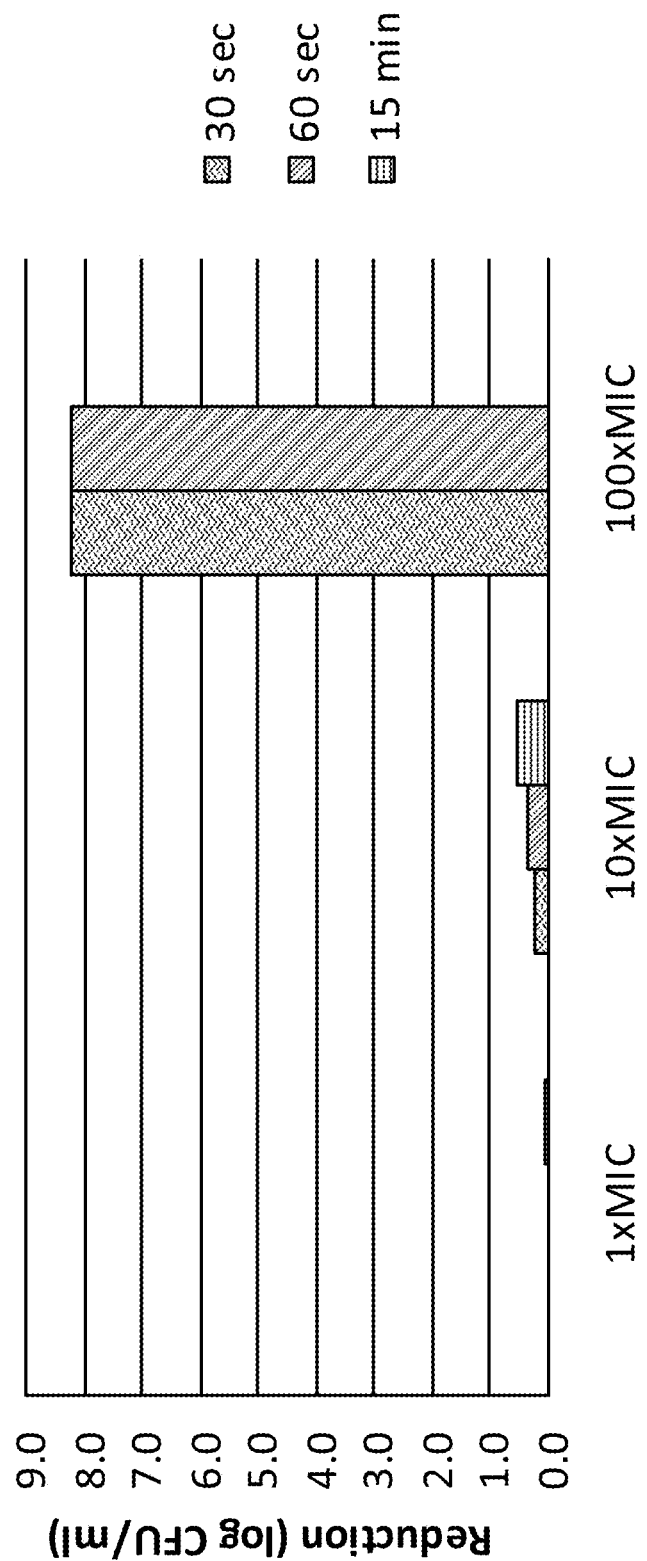

Furthermore, as demonstrated at FIGS. 3A and 3B, between 2 and 4 log reduction of *E. coli* ATCC 11229 growth is observed upon contacting the bacteria with two acids and pediocin or reuterin (Mix I or II) for 15 minutes at a concentration of 10× MIC. An 8 log reduction of *E. coli* ATCC 11229 growth is observed after only 30 or 60 seconds of contacting the bacteria with these compositions at a concentration of 100×MIC. A 8 log reduction of *S. aureus* ATCC 6538 growth is observed after 30 or 60 seconds when these compositions are used at a concentration of 100×MIC (FIGS. 4A and 4B). As such, the compositions could have a synergistic action against Gram-positive and Gram-negative bacteria and have a large spectrum of antimicrobial activity.

In an embodiment, the composition identified as Mix I (citric and lactic acids and pediocin) comprises citric acid in an amount from about 0.20 to 20% by weight or volume, lactic acid in an amount from about 0.10 to 10% by weight or volume and pediocin in an amount from about 40 to 4000 AU/ml. For example the composition could comprise 0.33, 3.3, 6.6, 13.2, 19.8, % by weight or volume of citric acid, 0.125, 1.25, 2.5, 5, 7.5 and 10% by weight or volume of lactic acid and 40, 400, 800, 1600, 2400, 3200 and 4000 AU/ml of pediocin.

In another embodiment, Mix I comprises citric acid in an amount of about 0.20% by weight or volume, lactic acid in an amount of about 0.10% by weight or volume and pediocin in an amount of about 40 AU/ml.

In another embodiment, Mix I comprises citric acid in an amount of about 20% by weight or volume, lactic acid in an amount of about 10% by weight or volume and pediocin in an amount of about 4000 AU/ml.

In one embodiment, the composition identified as Mix II (citric and lactic acids and reuterin) comprises citric acid in an amount from about 0.2 to 20% by weight or volume, lactic acid in an amount from about 0.10 to 10% by weight or volume and reuterin in an amount from about 1.28 to 128 AU/ml. For example the composition could comprise 0.33, 3.3, 6.6, 13.2, 19.8, % by weight or volume of citric acid, 0.125, 1.25, 2.5, 5, 7.5 and 10% by weight or volume of lactic acid and 1.28, 12.8, 25.6, 51.2, 76.8, 102.4, and 128 AU/ml of reuterin.

In another embodiment, Mix II comprises citric acid in an amount of about 0.2% by weight or volume, lactic acid in an amount of about 0.10% by weight or volume and reuterin in an amount of about 1.28 AU/ml.

In another embodiment, Mix II comprises citric acid in an amount of about 20% by weight or volume, lactic acid in an amount of about 10% by weight or volume and reuterin in an amount of about 128 AU/ml.

As shown at FIG. 5, acetic and lactic acids, pediocin and reuterin individually do not inhibit *E. Coli* ATCC 11229 bacterial growth as efficiently as Mix I (citric and lactic acids and pediocin) and Mix II (citric and lactic acids and reuterin). Similar results can be observed at FIG. 6 wherein Mix I (citric and lactic acids and pediocin) as well as Mix II (citric and lactic acids and reuterin) inhibit *Listeria ivanovii* HBP 28 bacterial growth.

The scope of the claims should not be limited by the specific embodiments set forth in the examples, but should be given the broadest interpretation consistent with the description as a whole.

Materials and Methods

1. Target Bacterial Strains, Media and Growth Conditions

The following bacterial strains were used:

| Strain | Source | Medium | Growth Temp (° C.) |
|---|---|---|---|
| *Pediococcus acidilactici* | Paul&Fliss Int. | MRS | 30 |
| *Lactobacillus reuteri* | ATCC 53608 | MRS | 37 |
| *Escherichia coli* | ATCC 11229 | TSB | 37 |
| *Escherichia coli* MC 4100 | La Rochelle | TSB | 37 |
| *Listeria ivanovii* | HPB 28 | TSB | 30 |
| *Staphylococcus aureus* subsp. *aureus* | ATCC 6538 | TSB | 37 |
| *Pseudomonas aeruginosa* | ATCC 15442 | TSB | 37 |
| *Salmonella enterica* | ATCC 14028 | TSB | 37 |
| *Enterococcus faecalis* | ATCC 27275 | TSB | 37 |
| *Listeria monocytogenes* | LSD 532 | TSB | 30 |
| *Listeria monocytogenes* LMA 1045 | Laval U | TSB | 30 |

All strains were maintained in 20% glycerol at −80° C. Strains were reactivated by at least three 24-h sub-cultures in the appropriate medium to obtain stock culture for experiments.

2. Natural Antimicrobial Compounds

Fresh pediocin extract was prepared according to known methods and for instance as described by (Naghmouchi et al. 2008).

Fresh reuterin extract was prepared from overnight culture of *Lactobacillus reuteri* available from ATCC as described by Vollenweider et al. 2004.

Acetic, citric, lactic and acids were used. Acetic acid was purchased from Sigma-Aldrich, Ontario, Canada and the others were obtained from Laboratoire MAT, Quebec City, Canada. The following table summarizes the characteristics of these organic acids.

| | Compound | | |
|---|---|---|---|
| | Acetic acid | Citric acid | Lactic acid |
| Formula | $C_2H_4O_2$ | $C_6H_8O_7$ | $C_3H_6O_3$ |
| pH at 20° C. | 2.4 | — | — |
| pH at 20% | — | 1.89 | 1.89 |
| Molar mass (g/mol) | 60.05 | 192.12 | 90.08 |
| Density ρ (g/mL) at 25° C. | 1.049 | powder | 1.209 |
| Purity of commercial preparation | 100% | 100% | 88% |
| Molarity at 20% mass/volume | 3.33 | 1.04 | 2.22 |

3. Microplate Microdilution Method

The inhibitory activity of the various antimicrobial compounds alone or in combination was assayed using the microtiter plate critical dilution method with two-fold serial dilutions in TSB (Turcotte et al., 2004). The 100-μL carry-over volume was drawn into the multi-channel pipette four times between each dilution. Wells were then seeded with 40 μL of target strain overnight culture diluted 1,000 fold. The plates (MIC-2000 U-Bottom Microtiter® Plates; Thermo Labsystems, Franklin, Mass., USA) were incubated at 30° C. for 18 h before reading the optical density at 650 nm using a Thermomax microplate reader (Molecular Devices, Opti-Resources, Charny, QC, Canada).

One arbitrary unit (AU) was defined as a 100-μL portion of the highest dilution of tested sample that inhibited growth in a well after 18 h of incubation (Daba et al, 1993). A well was considered positive (significant inhibition) when the optical density of the well was less than the half of the optical density of the positive control. The number of AU per ml is thus 20 n, where n=number of inhibited wells.

4. MIC and FIC Index Determinations

The MIC of each antimicrobial compound was determined using polystyrene 96-well micro-test plates (Becton Dickinson Labware, Lincoln Park, N.J.). A mid-log-phase culture of each sensitive strain was diluted 1/10,000 in fresh TSBYE to provide an initial bacteria concentration of 1-5× $10^5$ CFU/well. Two-fold serial dilutions of each antimicrobial compound were made by carrying over 100 μL in micro-plate wells pre-filled with 100 μL of TSYEB. Each well then received 25 μL of diluted culture as described by Mota-Meira et al. 2000. The micro-plates were incubated at 37° C. for 16 h and the optical density was read at 650 nm using a micro-plate reader. Control wells (inoculated with the tested culture without added inhibitor) and blank wells (containing un-inoculated broth with added inhibitor) were included. The MIC corresponds to the minimal inhibitory concentration of tested inhibitor giving complete inhibition of detectable growth (OD equal to OD of blank). The micro-dilution assay was repeated three times and results were presented as the median of the three repetitions. The antimicrobial activity of different combinations of compounds against their target strains was measured by calculating the FIC index using the checkerboard method with 96-well polystyrene micro-plates. Briefly, each well containing 120 μL of TSBYE medium with two compounds (60 μL each) received 120 μL of diluted bacterial suspension. The micro-plates were incubated at 37° C. for 18 h and the optical density was measured at 650 nm.

The FIC of an antimicrobial agent X is calculated as described by Schwalbe R et al. 2007.

$$FIC(X) = MIC(X)_{in\ combination}/MIC(X)_{alone}$$

The FIC index of a combination of agents A and B is the sum of their FIC (FIC index $=\Sigma FIC=FIC_A+FIC_B$). The interaction is considered synergistic if the FIC index is <0.5, moderate synergy if 0.5<FIC index 1.0, indifferent if 1.0<FIC index 4.0, and antagonistic if the FIC index >4.0.

The FIC index determination was repeated independently three times as shown at FIGS. 9 to 14.

5. Agar Diffusion Test

The agar well diffusion method previously described by Tagg et al. 1976 was applied as a rapid method to detect the inhibitory activity of the compounds directly (as a solution) or after immobilization on paper towel. Briefly, 25 mL of sterile TSB with 0.8% (w/v) agar was seeded with 150 μL of an overnight culture of one of the target sensitive strains and poured into a sterile Petri dish (Starstedt Inc., Montreal, Canada). The Petri dishes were kept for 20 min at room temperature under sterile conditions to allow agar solidification. Wells 7 mm in diameter were then cut in the solidified agar using the wide end of a sterile 5-mL pipette. Each well was filled with 80 μL of the compound or mixture to be tested. In the case of pre-soaked paper towel, circles 1 cm in diameter were cut and deposited directly on the solidified agar. All plates were incubated at 30° C. for 18 h and the diameter of the zone of inhibition was measured.

EXAMPLES

The inhibitory activity of the antimicrobial compounds was thus tested both in solution and after immobilization on paper towel provided by Cascades.

Antimicrobial activity of the antimicrobial compound solutions: Tables 1, 2 and FIGS. 9 to 14 present the FIC index obtained for compounds exhibiting significant synergistic effects against *E. coli* ATCC 11229 and *L. ivanovii* HPB28. The effects are variable. The greatest synergistic effect against *E. coli* ATCC 11229 was obtained for reuterin combined with lactic acid or citric acid (Table 1). Using *L. ivanovii* HPB28, all combinations containing pediocin, reuterin or Nisin were synergistic (Table 2 and FIGS. 9 to 14). As can also be shown from FIGS. 13 and 14, synergistic effects are observed when reuterin is combined with pediocin or Nisin Z. Based on these results and the MIC values obtained from screening tests using individual compounds two mixtures were formulated, the compositions of which are shown in Tables 3 and 4.

TABLE 1

Synergetic effects of selected natural compounds against *E. coli* ATCC 11229 based on FIC index calculation.

|  | Citric acid | Lactic acid | Reuterin | Pediocin PA-1 |
|---|---|---|---|---|
| Citric acid | — | 0.75 | 0.5 | 1 |
| Lactic acid | 0.75 | — | 0.5 | 0.75 |
| Reuterin | 0.5 | 0.5 | — | 0.75 |
| Pediocin PA-1 | 1 | 0.75 | 0.75 | — |

TABLE 2

Synergetic effects of selected natural compounds against *Listeria ivanovii* HPB28 based on FIC index calculation.

|  | Citric acid | Lactic acid | Reuterin | Pediocin PA-1 |
|---|---|---|---|---|
| Citric acid | — | 0.75 |  | 0.75 |
| Lactic acid | 0.75 | — | 0.75 | 0.75 |
| Reuterin | 0.625 | 0.75 | — | 0.75 |
| Pediocin PA-1 | 0.75 | 0.75 | 0.75 | — |

TABLE 3

Final concentration of Mix I and II determined on the inhibition activities and FIC indexes obtained with different inhibition compounds (in liquid form).

|  | Mix I Final | Mix II Final |
|---|---|---|
| Citric acid | 0.2% | 0.2% |
| Lactic acid | 0.1% | 0.1% |
| Reuterin | — | 1% (1.28 AU/ml) |
| Pediocin | 0.1% (40 AU/ml) | — |

The synergism of these mixtures against *E. coli* ATCC 11229 and *L. ivanovii* HPB28 was confirmed based on the growth curves obtained in the presence of the antimicrobial compounds either alone or in combination. For example, as shown in FIGS. 1A and 1B, inhibition of both *E. coli* ATCC 11229 and *L. ivanovii* HPB 28 was total with the citric acid, lactic acid and reuterin (Mix II). Only a partial and non-significant inhibition was observed when the three active compounds were each used alone at concentrations of 0.25%, 0.25% and 1.25% respectively. Similar results were obtained with Mix I with reuterin replaced by pediocin (FIG. 2).

Figure 7A:
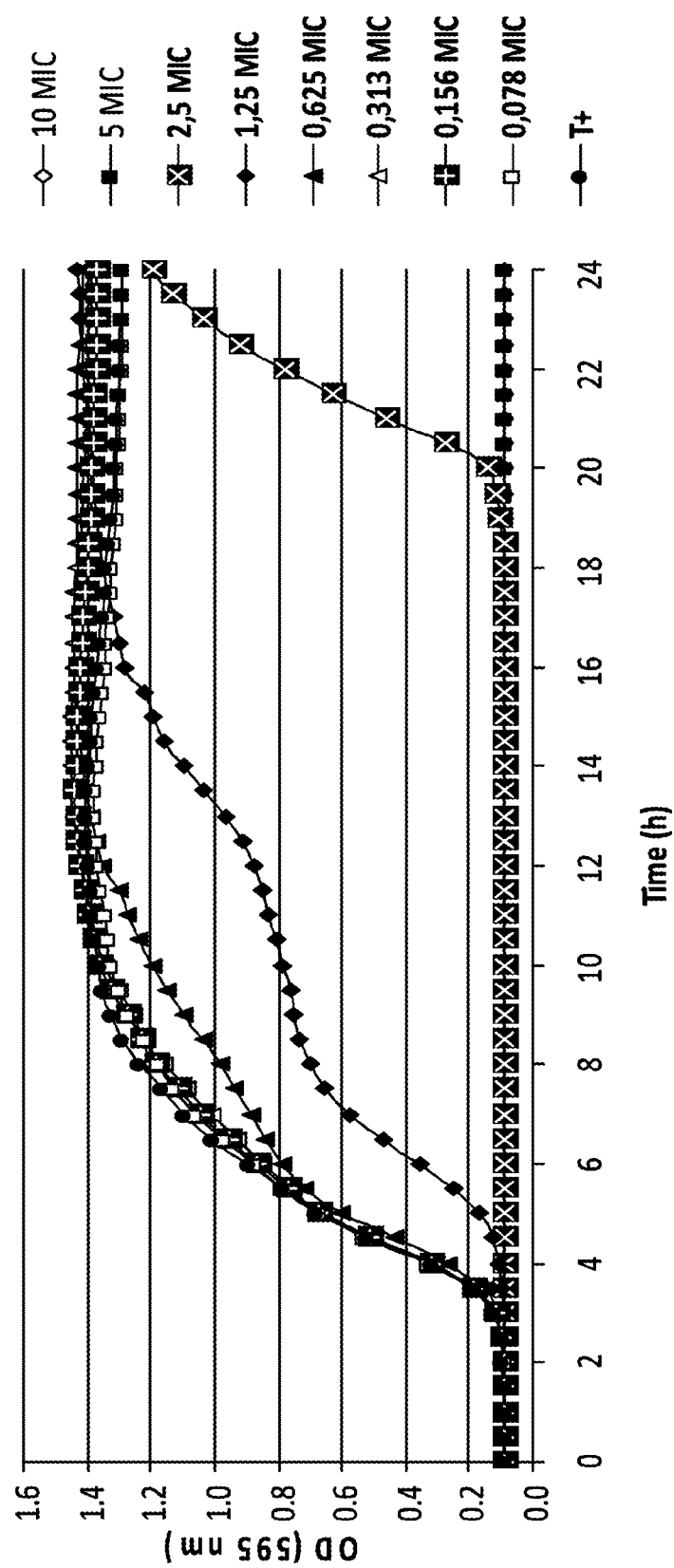
Figure 7B:
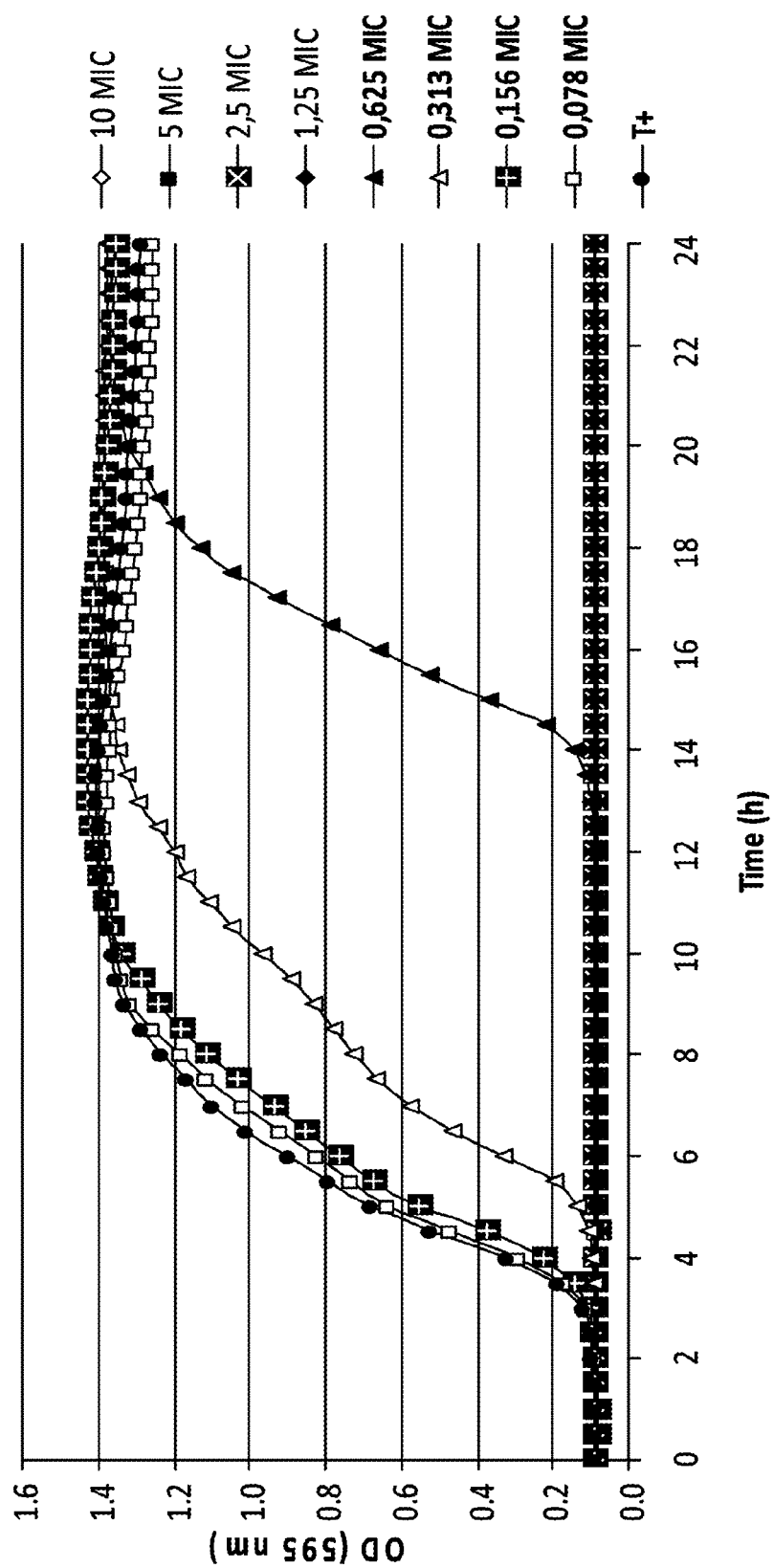
Figure 8A:
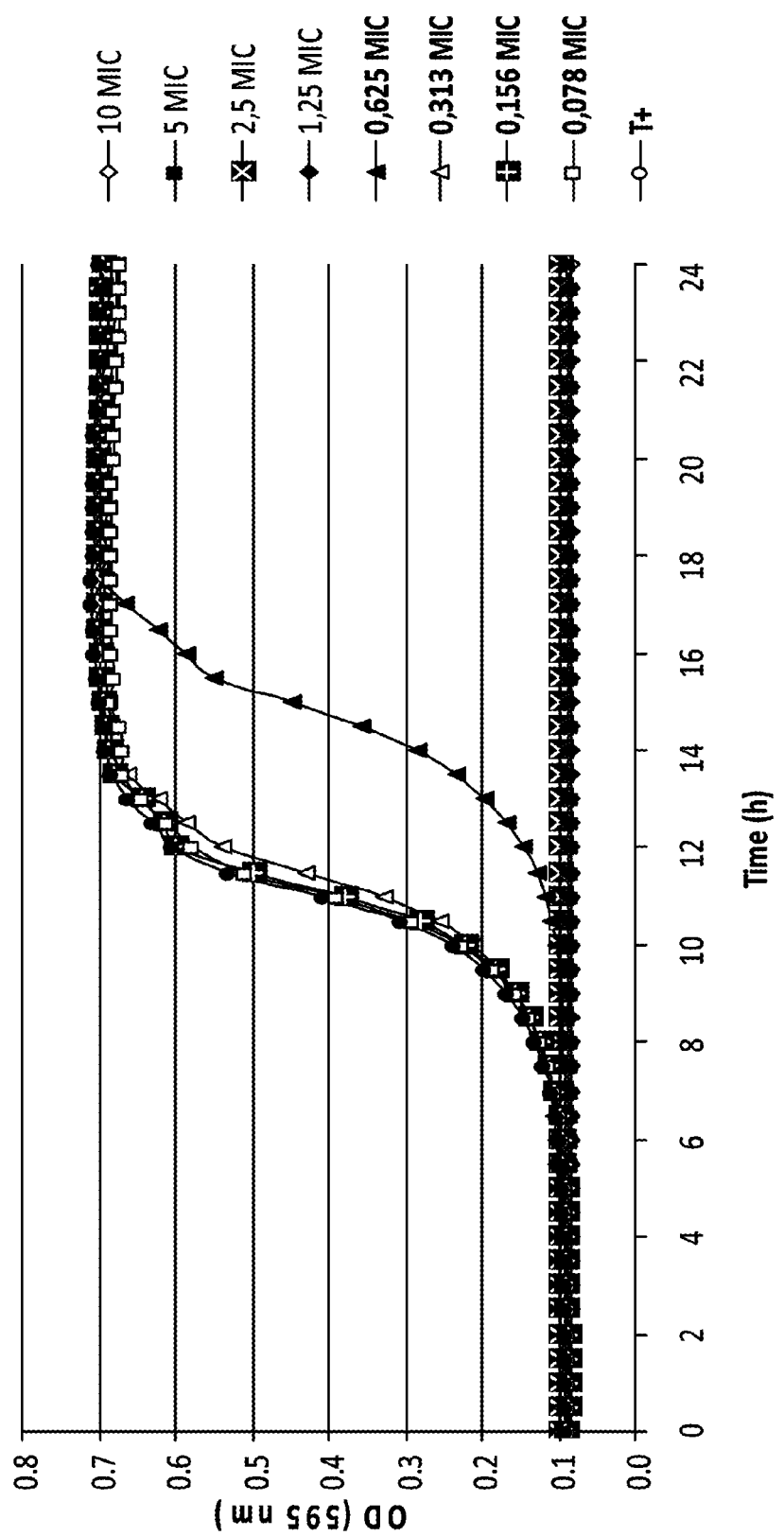
Figure 8B:
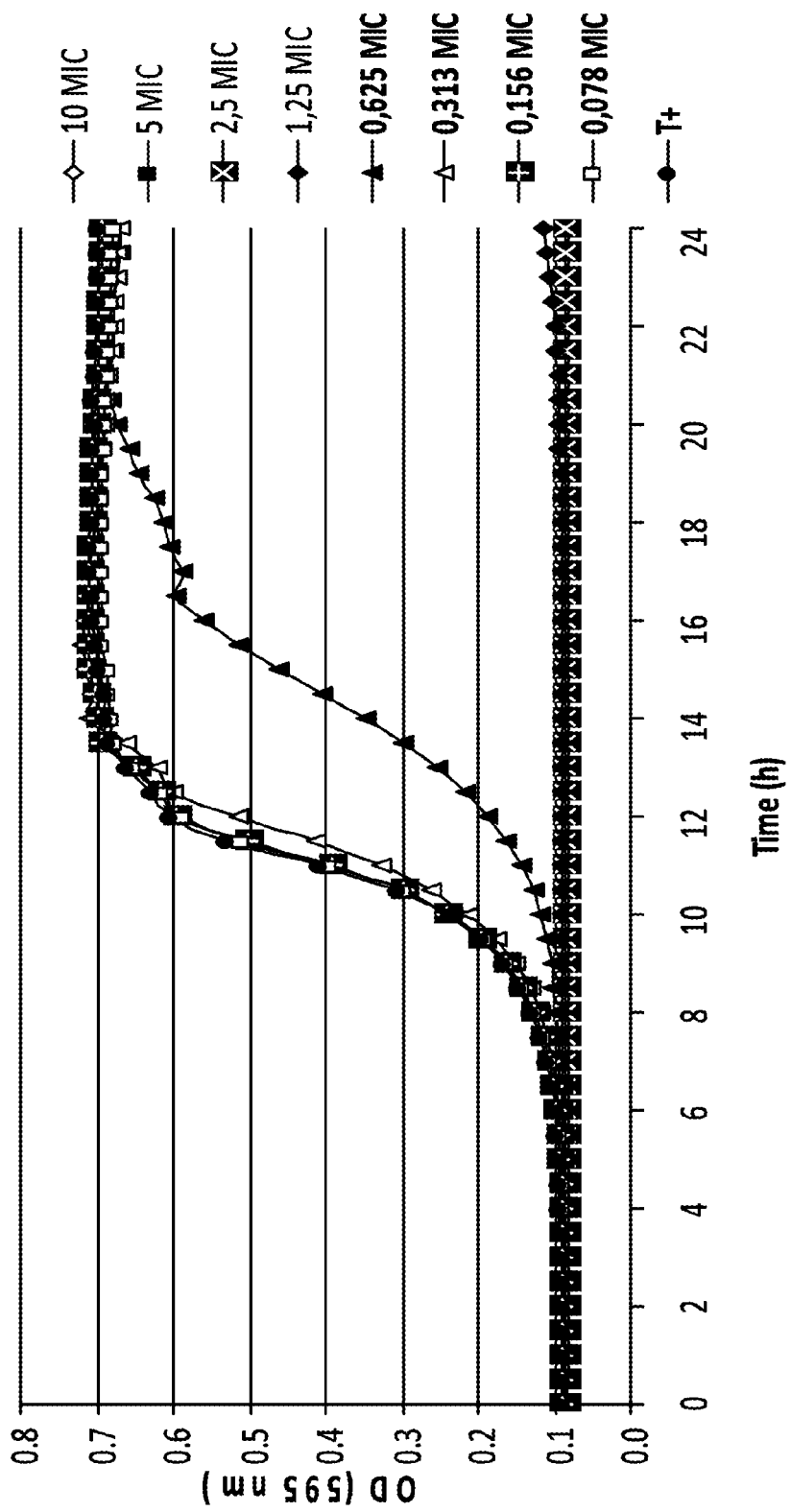

FIGS. 7A and 7B show the growth kinetics of *E. coli* ATCC 11229 as a function of the concentration of Mix I and II, expressed in terms of MIC. Inhibition of *E. coli* ATCC 11229 was total at 5 times the MIC. At a concentration equivalent to 0.625 MIC, inhibition lasted 14 hours only for Mix II, while lower concentrations were not inhibitory. In the case of *L. ivanovii* HPB28, total inhibition was observed at 1.25 times MIC for Mix I and II and no inhibition was observed with concentrations of 0.3 times or less (FIGS. 8A and 8B).

The inhibitory activity of the antimicrobial compounds was thus tested both in solution and after soaking on paper towel provided by Cascades.

2. Antimicrobial Activity of Paper Towel Pre-Soaked with the Mixtures

The aim of this experiment was to study the inhibition of bacterial growth by the antimicrobial Mix I and II in association with paper towels. This was of course based on the assumption that the active compounds would diffuse from the towels. Mix I and II were tested at 1, 10 and 100 times the MIC shown in Tables 3. As shown at FIGS. 5 and 6, significant inhibition (indicated by the clear inhibition zone around the paper) was obtained for both Mix at 100 times the MIC, against both *E. coli* ATCC 11229 and *L. ivanovii* HPB28. Inhibition of *Listeria* was significantly stronger with Mix I, which contains pediocin (FIG. 6A). On the other hand, no clear inhibition of any strain was observed at 10 times the MIC, even though this concentration was effective in the agar diffusion test. This is surprising since 8-log reduction of *E. coli* ATCC 11229 (FIGS. 3A and 3B) and *S. aureus* ATCC 6538 (FIGS. 4A and 4B) was obtained with both Mix at 100 times MIC after only 15 seconds of contact time between the bacteria and the Mix using AOAC 960.09 method (AOAC 2000). Similar results were obtained with *L. monocytogenes*, *E. faecalis* and *S. enterica*. At 10 times MIC, between 0.5-log and 5-log reductions was observed with a contact time of 15 minutes between the bacteria and the Mix, while no inhibition was observed with shorter contact times. At 1×MIC, no inhibition was obtained with a contact time of 15 minutes. The final compositions of Mix I and II, based on the results described above, are presented in Table 4.

TABLE 4

Final concentration of Mix I and II determined on the inhibition activities with different pre-soaked towel paper.

|  | Mix I Final | Mix II Final |
| --- | --- | --- |
| Citric acid | 20% | 20% |
| Lactic acid | 10% | 10% |
| Reuterin | — | 128 AU/ml |
| Pediocin | 4000 AU/ml | — |

REFERENCES

Saïd Ennahar, Toshihiro Sashihara, Kenji Sonomoto, Ayaaki Ishizaki 2000. Class IIa bacteriocins: biosynthesis, structure and activity. FEMS Microbiology Reviews Volume 24, Issue 1, pages 85-106, January 2000.
Hammami R, Zouhir A, Le Lay C, Ben Hamida J, Fliss I. BACTIBASE second release: a database and tool platform for bacteriocin characterization. BMC Microbiol. 2010 Jan. 27; 10:22. PubMed PMID: 20105292.
Hammami R, Zouhir A, Ben Hamida J, Fliss I. BACTIBASE: a new web-accessible database for bacteriocin characterization. BMC Microbiol. 2007 Oct. 17; 7:89.
Turcotte C, Lacroix C, Kheadr E, Grignon L, Fliss I. A rapid turbidometric microplate bioassay for accurate quantification of lactic acid bacteria bacteriocins. Int J Food Microbiol. 2004 Feb. 1; 90(3):283-93.
Benech R O, Kheadr E E, Lacroix C, Fliss I. Antibacterial activities of nisin Z encapsulated in liposomes or produced in situ by mixed culture during cheddar cheese ripening. Appl Environ Microbiol. 2002 November; 68(11):5607-19.
Mota-Meira M, LaPointe G, Lacroix C, Lavoie M C. MICs of mutacin B-Ny266, nisin A, vancomycin, and oxacillin against bacterial pathogens. Antimicrob Agents Chemother. 2000 January;44(1):24-9. Barchiesi et al (2001).
Daba, Hocine; Lacroix, Christophe; Huang, June 1993. Influence of growth conditions on production and activity of mesenterocin 5 by a strain of *Leuconostoc mesenteroides* Applied Microbiology and Biotechnology (1993) 39: 166-173.
Tagg J R, Dajani A S, Wannamaker L W. 1976. Bacteriocins of gram-positive bacteria. Bacteriol. Rev 40:722-56.
Vollenweider S, Lacroix C: 2004. 3-hydroxypropionaldehyde: applications and perspectives of biotechnological production. Appl Microbiol Biotechnol. 64(1):16-27.
*Benebank.* Nucleic Acids Research, 2011 January; 39(Database issue):D32-.7 AOAC International. 2000. AOAC official method 960.09. Germicidal and detergent sanitizing action of disinfectants.
Naghmouchi K, Fliss I, Drider D, Lacroix C. 2008. Pediocin PA-1 production during repeated-cycle batch culture of immobilized *Pediococcus acidilactici* UL5 cells. J Biosci Bioeng. 105(5):513-7.
Antimicrobial Susceptibility Testing Protocols. 2007. Kindle Edition Richard Schwalbe (Editor), Lynn Steele-Moore (Editor), Avery C. Goodwin (Editor) CRC Press, NY, usa.
Abee T., 1995. Pore-forming bacteriocins of Gram$^+$ bacteria and self-protection mechanisms of producer organisms. FEMS Microbiol. Lett., 129, 1-9.
Cutter, C. N., J. L. Willett, and G. R Siragusa. 2001. Improved antimicrobial activity of nisin-incorporated polymer films by formulation change and addition of food grade chelator. Lett. Appl. Microbiol. 33:325-328.
Allende et al. Growth and bacteriocin production by lactic acid bacteria in vegetable broth and their effectiveness at reducing. 2007. Food Microbiology, 24, 7: 759-766.
Nilsson L, Nielsen M K, Ng Y, Gram L. 2002. Role of acetate in production of an autoinducible class IIa bacteriocin in *Carnobacterium piscicola* A9b. Appl Environ Microbiol. 68, 5:2251-60.

What is claimed is:

1. An antimicrobial composition comprising about 200 AU/ml of pediocin, about 0.5% by weight or volume lactic acid and about 1.0% by weight or volume of citric acid.

2. The antimicrobial composition of claim 1, wherein the antimicrobial composition has an antimicrobial activity against Gram-positive and Gram-negative bacteria.

3. The antimicrobial composition of claim 2, wherein the Gram-positive bacteria is *Enterococcus faecium*, *Staphylococcus aureus*, *Listeria monocytogenes* Scott3, *Corynebacterium*, *Streptococcus* M3, *Streptococcus agalactiae*, *Streptococcus* sp, or *Clostridium difficile*.

4. The antimicrobial composition of claim 2, wherein the Gram-negative bacteria is *Aeromonas*, *Escherichia coli* O157:H7, *Escheria coli*, *Pseudomonas fluorescens*, *Serratia marcescens*, *Salmonella* sp, *Pseudomonas aeroginosa*, *Pseudomonas euroginosa*, *Erwinia*, *Yersinia enterocolitica* or *Aeromonas Hydrophila*.

5. The composition of any claim 1, wherein the pediocin is pediocin PA-1.

6. The antimicrobial composition of claim 1, further comprising a surfactant.

7. The antimicrobial composition of claim 1 in form of a foam, ointment, gel, liquid, spray or powder.

8. A cellulosic substrate comprising the antimicrobial composition as defined in claim 1.

9. A food packaging comprising the antimicrobial composition as defined in claim 1.

10. The food packaging of claim 9, wherein the food packaging is a film, resin, liner, absorbent pad, plastic, shrink bag, shrink wrap, plastic wrap, Styrofoam™, carton, or cellulosic substrate.

11. A method for sanitizing and/or disinfecting a surface, comprising applying an effective antimicrobial amount of the antimicrobial composition as defined in claim 1 to the surface.

12. The method of claim 11, wherein the surface is the surface of an object, food, food plant, a body part or a food packaging.

13. The method of claim 12, wherein the food packaging is a film, resin, liner, absorbent pad, plastic, shrink bag, shrink wrap, plastic wrap, Styrofoam™, carton, or cellulosic substrate.

* * * * *